(12) United States Patent
Gera et al.

(10) Patent No.: US 11,389,252 B2
(45) Date of Patent: Jul. 19, 2022

(54) ROTATING MARKER FOR IMAGE GUIDED SURGERY

(71) Applicant: Augmedics Ltd., Yokneam Illit (IL)

(72) Inventors: Tomer Gera, Kfar Tavor (IL); Nissan Elimelech, Beerotaim (IL); Nitzan Krasney, Haifa (IL); Stuart Wolf, Yokneam (IL)

(73) Assignee: AUGMEDICS LTD., Yokneam (IL)

( * ) Notice: Subject to any disclaimer, the term of this patent is extended or adjusted under 35 U.S.C. 154(b) by 58 days.

(21) Appl. No.: 16/901,026

(22) Filed: Jun. 15, 2020

(65) Prior Publication Data

US 2021/0386482 A1 Dec. 16, 2021

(51) Int. Cl.
*A61B 34/20* (2016.01)
*A61B 34/10* (2016.01)
*A61B 90/00* (2016.01)
*G06T 19/00* (2011.01)

(52) U.S. Cl.
CPC .............. *A61B 34/20* (2016.02); *A61B 34/10* (2016.02); *A61B 90/39* (2016.02); *G06T 19/003* (2013.01); *G06T 19/006* (2013.01); *A61B 2034/107* (2016.02); *A61B 2034/2055* (2016.02); *A61B 2090/3904* (2016.02); *G06T 2210/41* (2013.01)

(58) Field of Classification Search
CPC ......... A61B 34/20; A61B 34/10; A61B 90/39; A61B 2034/107; A61B 2034/2055; A61B 2090/3904; A61B 2017/00477; A61B 2090/365; A61B 2090/371; A61B 2090/372; A61B 2090/3916; A61B 2090/3983; A61B 2090/3991; A61B 90/36; A61B 2090/502; G06T 19/003; G06T 19/006; G06T 2210/41
See application file for complete search history.

(56) References Cited

U.S. PATENT DOCUMENTS

| 4,863,238 A | 9/1989 | Brewster |
| 5,441,042 A | 8/1995 | Putman |
| 5,792,046 A | 8/1998 | Dobrovolny |
| 5,841,507 A | 11/1998 | Barnes et al. |

(Continued)

FOREIGN PATENT DOCUMENTS

| CA | 3022448 A1 * | 2/2018 | ............. A61B 34/10 |
| CA | 3022448 A1 | 2/2018 | |

(Continued)

OTHER PUBLICATIONS

International Applicaton # PCT/IB2020/056893 Search Report dated Nov. 9, 2020.

(Continued)

*Primary Examiner* — Maurice L. McDowell, Jr.
(74) *Attorney, Agent, or Firm* — Kligler & Associates Patent Attorneys Ltd

(57) ABSTRACT

A marker for image guided surgery, consisting of a base, having a base axis, connecting to a clamp; and an alignment target. The alignment target includes a target region having an alignment pattern formed thereon, and a socket connected to the target region and configured to fit rotatably to the base, whereby the alignment target is rotatable about the base axis. The alignment target also includes an optical indicator for the socket indicating an angle of orientation of the alignment target about the base axis.

19 Claims, 13 Drawing Sheets

(56) References Cited

U.S. PATENT DOCUMENTS

| | | | |
|---|---|---|---|
| 6,006,126 A | 12/1999 | Cosman | |
| 6,256,529 B1 | 7/2001 | Holupka et al. | |
| 6,314,310 B1 | 11/2001 | Ben-Haim et al. | |
| 6,609,022 B2 | 8/2003 | Vilsmeier et al. | |
| 6,610,009 B2 | 8/2003 | Person | |
| 6,675,040 B1 | 1/2004 | Cosman | |
| 6,757,068 B2 | 6/2004 | Foxlin | |
| 6,856,826 B2 | 2/2005 | Seeley et al. | |
| 6,891,518 B2 | 5/2005 | Sauer et al. | |
| 6,919,867 B2 | 7/2005 | Sauer | |
| 7,043,961 B2 | 5/2006 | Pandey et al. | |
| 7,107,091 B2 | 9/2006 | Jutras et al. | |
| 7,171,255 B2 | 1/2007 | Holupka et al. | |
| 7,229,078 B2 | 6/2007 | Lechot | |
| 7,320,556 B2 | 1/2008 | Vagn-Erik | |
| 7,364,314 B2 | 4/2008 | Nilsen et al. | |
| 7,435,219 B2 | 10/2008 | Kim | |
| 7,493,153 B2 | 2/2009 | Ahmed et al. | |
| 7,556,428 B2 | 7/2009 | Sukovic et al. | |
| 7,630,753 B2 | 12/2009 | Simon et al. | |
| 7,719,769 B2 | 5/2010 | Sugihara et al. | |
| 7,768,702 B2 | 8/2010 | Hirose et al. | |
| 7,769,236 B2 | 8/2010 | Fiala | |
| 7,774,044 B2 | 8/2010 | Sauer et al. | |
| 7,840,256 B2 | 11/2010 | Lakin et al. | |
| 7,857,271 B2 | 12/2010 | Lees | |
| 7,874,686 B2 | 1/2011 | Rossner et al. | |
| 7,881,770 B2 | 2/2011 | Melkent et al. | |
| 7,993,353 B2 | 8/2011 | Robner et al. | |
| 8,271,069 B2 | 9/2012 | Jascob et al. | |
| 8,306,305 B2 | 11/2012 | Porat et al. | |
| 8,386,022 B2 | 2/2013 | Jutras et al. | |
| 3,690,776 A1 | 4/2014 | Razzaque et al. | |
| 8,692,845 B2 | 4/2014 | Fedorovskaya et al. | |
| 8,836,768 B1 | 9/2014 | Rafii et al. | |
| 8,848,977 B2 | 9/2014 | Bammer et al. | |
| 8,950,877 B2 | 2/2015 | Northey et al. | |
| 9,149,317 B2 | 10/2015 | Arthur et al. | |
| 9,179,984 B2 | 11/2015 | Teichman et al. | |
| 9,220,573 B2 | 12/2015 | Kendrick et al. | |
| 9,378,558 B2 | 6/2016 | Kajiwara et al. | |
| 9,456,878 B2 | 10/2016 | Macfarlane et al. | |
| 9,495,585 B2 | 11/2016 | Bicer et al. | |
| 9,498,231 B2 | 11/2016 | Haider et al. | |
| 9,532,849 B2 | 1/2017 | Anderson et al. | |
| 9,538,962 B1 | 1/2017 | Hannaford et al. | |
| 9,710,968 B2 | 7/2017 | Dillavou et al. | |
| 9,724,165 B2 | 8/2017 | Arata et al. | |
| 9,757,087 B2 | 9/2017 | Simon et al. | |
| 9,844,413 B2 | 12/2017 | Daon et al. | |
| 9,872,733 B2 | 1/2018 | Shoham et al. | |
| 9,886,552 B2 | 2/2018 | Dillavou et al. | |
| 9,892,564 B1 | 2/2018 | Cvetko et al. | |
| 9,898,866 B2 | 2/2018 | Fuchs et al. | |
| 9,928,629 B2 | 3/2018 | Benishti et al. | |
| 9,940,750 B2 | 4/2018 | Dillavou et al. | |
| 9,943,374 B2 | 4/2018 | Merritt et al. | |
| 9,959,629 B2 | 5/2018 | Dillavou et al. | |
| 10,010,379 B1 | 7/2018 | Gibby et al. | |
| 10,022,065 B2 | 7/2018 | Ben-Yishai et al. | |
| 10,022,104 B2 | 7/2018 | Sell et al. | |
| 10,034,713 B2 | 7/2018 | Yang et al. | |
| 10,080,616 B2 | 9/2018 | Wilkinson et al. | |
| 10,085,709 B2 | 10/2018 | Lavallee et al. | |
| 10,108,833 B2 | 10/2018 | Hong et al. | |
| 10,134,166 B2 | 11/2018 | Benishti et al. | |
| 10,166,079 B2 | 1/2019 | McLachlin et al. | |
| 10,181,361 B2 | 1/2019 | Dillavou et al. | |
| 10,194,131 B2 | 1/2019 | Casas | |
| 10,194,993 B2 | 2/2019 | Roger et al. | |
| 10,251,724 B2 | 4/2019 | McLachlin et al. | |
| 10,296,805 B2 | 5/2019 | Yang et al. | |
| 10,420,626 B2 | 9/2019 | Tokuda et al. | |
| 10,463,434 B2 | 11/2019 | Siegler et al. | |
| 10,504,231 B2 | 12/2019 | Fiala | |
| 10,537,395 B2 | 1/2020 | Perez | |
| 10,573,087 B2 | 2/2020 | Gallop et al. | |
| 10,586,400 B2 | 3/2020 | Douglas | |
| 10,792,110 B2 | 10/2020 | Leung et al. | |
| 10,799,316 B2 | 10/2020 | Sela et al. | |
| 10,838,206 B2 | 11/2020 | Fortin-Deschenes et al. | |
| 10,841,556 B2 | 11/2020 | Casas | |
| 10,842,461 B2 | 11/2020 | Johnson et al. | |
| 10,893,260 B2 | 1/2021 | Trail et al. | |
| 11,058,390 B1 | 7/2021 | Douglas | |
| 2002/0082498 A1 | 6/2002 | Wendt et al. | |
| 2003/0156144 A1 | 8/2003 | Morita | |
| 2003/0210812 A1 | 11/2003 | Khamene et al. | |
| 2003/0225329 A1 | 12/2003 | Rossner et al. | |
| 2004/0030237 A1 | 2/2004 | Lee et al. | |
| 2004/0138556 A1 | 7/2004 | Cosman | |
| 2005/0024586 A1 | 2/2005 | Teiwes et al. | |
| 2005/0119639 A1 | 6/2005 | McCombs et al. | |
| 2006/0176242 A1 | 8/2006 | Jaramaz et al. | |
| 2008/0007645 A1 | 1/2008 | McCutchen | |
| 2008/0085033 A1 | 4/2008 | Haven et al. | |
| 2008/0183065 A1 | 7/2008 | Goldbach | |
| 2008/0221625 A1 | 9/2008 | Hufner et al. | |
| 2008/0262812 A1 | 10/2008 | Arata et al. | |
| 2009/0018437 A1 | 1/2009 | Cooke | |
| 2009/0227847 A1 | 9/2009 | Tepper et al. | |
| 2010/0114110 A1 | 5/2010 | Taft et al. | |
| 2010/0149073 A1 | 6/2010 | Chaum et al. | |
| 2011/0004259 A1 | 1/2011 | Stallings et al. | |
| 2011/0098553 A1 | 4/2011 | Robbins et al. | |
| 2011/0105895 A1 | 5/2011 | Komblau et al. | |
| 2011/0216060 A1 | 9/2011 | Weising et al. | |
| 2011/0245625 A1 | 10/2011 | Trovato et al. | |
| 2011/0254922 A1 | 10/2011 | Schaerer et al. | |
| 2012/0014608 A1 | 1/2012 | Watanabe et al. | |
| 2012/0068913 A1 | 3/2012 | Bar-Zeev et al. | |
| 2012/0078236 A1* | 3/2012 | Schoepp | A61B 34/20 606/1 |
| 2012/0109151 A1 | 5/2012 | Maier-Hein et al. | |
| 2012/0143050 A1 | 6/2012 | Heigl | |
| 2012/0182605 A1 | 7/2012 | Hall et al. | |
| 2012/0216411 A1 | 8/2012 | Wevers et al. | |
| 2012/0289777 A1 | 11/2012 | Chopra et al. | |
| 2012/0306850 A1 | 12/2012 | Balan et al. | |
| 2012/0320100 A1 | 12/2012 | Machida et al. | |
| 2013/0002928 A1 | 1/2013 | Imai | |
| 2013/0009853 A1 | 1/2013 | Hesselink et al. | |
| 2013/0050258 A1 | 2/2013 | Liu et al. | |
| 2013/0050833 A1 | 2/2013 | Lewis et al. | |
| 2013/0057581 A1 | 3/2013 | Meier | |
| 2013/0083009 A1 | 4/2013 | Geisner et al. | |
| 2013/0106833 A1 | 5/2013 | Fun | |
| 2013/0135734 A1 | 5/2013 | Shafer et al. | |
| 2013/0209953 A1 | 8/2013 | Arlinsky et al. | |
| 2013/0234914 A1 | 9/2013 | Fujimaki | |
| 2013/0234935 A1 | 9/2013 | Griffith | |
| 2013/0237811 A1 | 9/2013 | Mihailescu et al. | |
| 2013/0249787 A1 | 9/2013 | Morimota | |
| 2013/0249945 A1 | 9/2013 | Kobayashi | |
| 2013/0265623 A1 | 10/2013 | Sugiyama et al. | |
| 2013/0267838 A1 | 10/2013 | Fronk et al. | |
| 2013/0278635 A1 | 10/2013 | Maggiore | |
| 2013/0300760 A1 | 11/2013 | Sugano et al. | |
| 2013/0342571 A1 | 12/2013 | Kinnebrew et al. | |
| 2014/0088402 A1 | 3/2014 | Xu | |
| 2014/0088990 A1 | 3/2014 | Nawana et al. | |
| 2014/0104505 A1 | 4/2014 | Koenig | |
| 2014/0114173 A1 | 4/2014 | Bar-Tal et al. | |
| 2014/0142426 A1 | 5/2014 | Razzaque et al. | |
| 2014/0168261 A1 | 6/2014 | Margolis et al. | |
| 2014/0176661 A1 | 6/2014 | Smurro et al. | |
| 2014/0177023 A1 | 6/2014 | Gao et al. | |
| 2014/0189508 A1 | 7/2014 | Granchi et al. | |
| 2014/0198129 A1 | 7/2014 | Liu et al. | |
| 2014/0240484 A1 | 8/2014 | Kodama et al. | |
| 2014/0243614 A1 | 8/2014 | Rothberg et al. | |
| 2014/0256429 A1 | 9/2014 | Kobayashi et al. | |
| 2014/0266983 A1 | 9/2014 | Christensen | |
| 2014/0268356 A1 | 9/2014 | Bolas et al. | |

(56) References Cited

U.S. PATENT DOCUMENTS

| | | |
|---|---|---|
| 2014/0270505 A1 | 9/2014 | McCarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0300967 A1 | 10/2014 | Tilleman et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0340286 A1 | 11/2014 | Machida et al. |
| 2014/0361956 A1 | 12/2014 | Mikhailov et al. |
| 2015/0005772 A1 | 1/2015 | Anglin et al. |
| 2015/0018672 A1 | 1/2015 | Blumhofer et al. |
| 2015/0070347 A1 | 3/2015 | Hofmann et al. |
| 2015/0150641 A1 | 6/2015 | Daon et al. |
| 2015/0209119 A1* | 7/2015 | Theodore ............... A61B 34/20 600/424 |
| 2015/0297314 A1 | 10/2015 | Fowler et al. |
| 2015/0305828 A1 | 10/2015 | Park et al. |
| 2015/0351863 A1 | 12/2015 | Plassky et al. |
| 2015/0366620 A1 | 12/2015 | Cameron et al. |
| 2016/0103318 A1 | 4/2016 | Du et al. |
| 2016/0125603 A1 | 5/2016 | Tanji |
| 2016/0175064 A1 | 6/2016 | Stenile et al. |
| 2016/0178910 A1 | 6/2016 | Gudicell et al. |
| 2016/0191887 A1 | 6/2016 | Casas |
| 2016/0223822 A1 | 8/2016 | Harrison et al. |
| 2016/0256223 A1 | 9/2016 | Haimer et al. |
| 2016/0302870 A1 | 10/2016 | Wilkinson et al. |
| 2016/0324583 A1 | 11/2016 | Kheradpr et al. |
| 2016/0339337 A1 | 11/2016 | Ellsworth et al. |
| 2017/0027650 A1 | 2/2017 | Merck et al. |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0014119 A1 | 6/2017 | Capote et al. |
| 2017/0164919 A1 | 6/2017 | LaVallee et al. |
| 2017/0164920 A1 | 6/2017 | Lavallee et al. |
| 2017/0178375 A1 | 6/2017 | Benishti et al. |
| 2017/0239015 A1 | 8/2017 | Sela et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0348055 A1 | 12/2017 | Salcedo et al. |
| 2017/0367766 A1 | 12/2017 | Mahfouz |
| 2017/0367771 A1 | 12/2017 | Tako et al. |
| 2018/0003981 A1 | 1/2018 | Urey |
| 2018/0018791 A1 | 1/2018 | Guoyi |
| 2018/0028266 A1 | 2/2018 | Barnes et al. |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0133871 A1 | 5/2018 | Farmer |
| 2018/0153626 A1 | 6/2018 | Yang et al. |
| 2018/0185100 A1 | 7/2018 | Weinstein et al. |
| 2018/0193097 A1 | 7/2018 | McLachlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0317803 A1 | 11/2018 | Ben-Yishai et al. |
| 2018/0318035 A1 | 11/2018 | McLachlin et al. |
| 2019/0000372 A1* | 1/2019 | Gullotti ............ A61B 17/7086 |
| 2019/0015163 A1 | 1/2019 | Abhari et al. |
| 2019/0038362 A1 | 2/2019 | Nash et al. |
| 2019/0043238 A1 | 2/2019 | Benishti et al. |
| 2019/0046272 A1 | 2/2019 | Zoabi et al. |
| 2019/0046276 A1 | 2/2019 | Inglese et al. |
| 2019/0080515 A1 | 3/2019 | Geri et al. |
| 2019/0105116 A1 | 4/2019 | Johnson et al. |
| 2019/0175228 A1 | 6/2019 | Elimelech et al. |
| 2019/0192230 A1 | 6/2019 | Siemionow et al. |
| 2020/0085511 A1* | 3/2020 | Oezbek ................. A61B 34/10 |
| 2020/0100847 A1* | 4/2020 | Siegler ................. A61B 5/1127 |
| 2020/0129136 A1 | 4/2020 | Harding et al. |
| 2020/0129264 A1* | 4/2020 | Onativia Bravo ..... A61B 90/90 |
| 2020/0138518 A1 | 5/2020 | Lang |
| 2020/0163723 A1 | 5/2020 | Wolf et al. |
| 2020/0163739 A1 | 5/2020 | Messinger et al. |
| 2020/0188034 A1 | 6/2020 | Lequette et al. |
| 2020/0237459 A1 | 7/2020 | Racheli et al. |
| 2020/0321099 A1 | 10/2020 | Holladay et al. |
| 2020/0337780 A1* | 10/2020 | Winkler ................. A61B 34/20 |
| 2020/0388075 A1 | 12/2020 | Kazanzides et al. |
| 2021/0004956 A1 | 1/2021 | Book et al. |
| 2021/0169504 A1* | 6/2021 | Brown .................. A61B 90/13 |
| 2021/0298835 A1* | 9/2021 | Wang ........................ G06T 7/70 |

FOREIGN PATENT DOCUMENTS

| | | |
|---|---|---|
| CN | 101379412 B | 3/2009 |
| CN | 103106348 A | 5/2013 |
| CN | 111915696 A | 11/2020 |
| CN | 112489047 B | 3/2021 |
| DE | 202004011567 U1 | 11/2004 |
| DE | 102014008153 A1 | 10/2014 |
| EP | 1640750 A1 | 3/2006 |
| EP | 3216416 A1 | 9/2017 |
| GB | 2507314 A | 4/2014 |
| KR | 20140120155 A | 10/2014 |
| WO | 03034705 A2 | 4/2003 |
| WO | 2007051304 A1 | 5/2007 |
| WO | 2007115826 A2 | 10/2007 |
| WO | 2008103383 A1 | 8/2008 |
| WO | 2010067267 A1 | 6/2010 |
| WO | 2013112554 A1 | 8/2013 |
| WO | 2014024188 A1 | 2/2014 |
| WO | 2014037953 A2 | 3/2014 |
| WO | 2014113455 A1 | 7/2014 |
| WO | 2014125789 A1 | 8/2014 |
| WO | 2014167563 A1 | 10/2014 |
| WO | 2014174067 A1 | 10/2014 |
| WO | 2015058816 A1 | 4/2015 |
| WO | 2018073452 A1 | 4/2018 |
| WO | 2019211741 A1 | 11/2019 |

OTHER PUBLICATIONS

U.S. Appl. No. 16/200,144 Office Action dated Dec. 28, 2020.
International Application # PCT/IB2020/060017 Search Report dated Jan. 7, 2021.
Wolf et al., U.S. Appl. No. 16/524,258, filed Jul. 29, 2019.
Wolf et al., U.S. Appl. No. 16/200,144, filed Nov. 26, 2018.
U.S. Appl. No. 16/724,297 Office Action dated Jan. 26, 2021.
U.S. Appl. No. 16/419,023 Office Action dated Jul. 22, 2021.
Lumus Ltd., "DK-32 See-through Wearable Display Development Kit", Rehovot, Israel, pp. 1-2, Dec. 24, 2013.
Liao et al., '3-D Augmented Reality for MRI-Guided Surgery Using Integral Videography Autostereoscopic Image Overlay', IEEE Transactions on Biomedical Engineering, vol. 57, No. 6, pp. 1476-1486, Feb. 17, 2010.
Hainich et al., "Near-Eye displays", Chapter 10 of Displays: Fundamentals and Applications, CRC press, pp. 439-504, Jul. 5, 2011.
Brainlab—Image Registration Options Enhanced Visualization Leveraging More Data , pp. 1-4, Feb. 2019.
Liu et al., "Marker orientation in fiducial registration", Medical Imaging 2003: Image Processing, Proceedings of SPIE vol. 5032, pp. 1176-1185, 2003.
Fingas, "Fraunhofer iPad app guides liver surgery through augmented reality", pp. 1-6, Aug. 22, 2013.
Sagitov et al., "Comparing Fiducial Marker Systems in the Presence of Occlusion", International Conference on Mechanical, System and Control Engineering (ICMSC), pp. 1-6, 2017.
Elimelech et al., U.S. Appl. No. 16/724,297, filed Dec. 22, 2019.
Elimelech et al., U.S. Appl. No. 16/524,258, filed Jul. 22, 2019.
U.S. Appl. No. 16/200,144 Office Action dated Aug. 19, 2021.
International Application # PCT/IB2021/055242 Search Report dated Oct. 7, 2021.

(56) References Cited

OTHER PUBLICATIONS

U.S. Appl. No. 16/724,297 Office Action dated Nov. 4, 2021.
JP Application # 2021525186 Office Action dated Dec. 1, 2021.
EP Application # 19796580 Search Report dated Dec. 20, 2021.
International Application No. PCT/IB2021/058088 Search Report dated Dec. 20, 2021.
CN Application No. 2019800757525 Office Action dated Mar. 1, 2022.
U.S. Appl. No. 16/200,144 Office Action dated Mar. 15, 2022.
U.S. Appl. No. 16/419,023 Office Action dated Mar. 1, 2022.
EP Application No. 16767845.7 Office Action dated Apr. 29, 2022.
U.S. Appl. No. 16/524,258 Office Action dated Apr. 11, 2022.
Lorensen et al., "Marching Cubes: A High Resolution 3D Surface Construction Algorithm," ACM SIGGRAPH '87, Computer Graphics, vol. 21, No. 4, pp. 163-169, Jul. 1987.
Wikipedia, "Marching Cubes," pp. 1-4, last edited Sep. 4, 2021.
Milletari et al., "V-Net: fully Convolutional Neural Networks for Volumetric Medical Image Segmentation," arXiv:1606.04797v1, pp. 1-11, Jun. 15, 2016.

\* cited by examiner

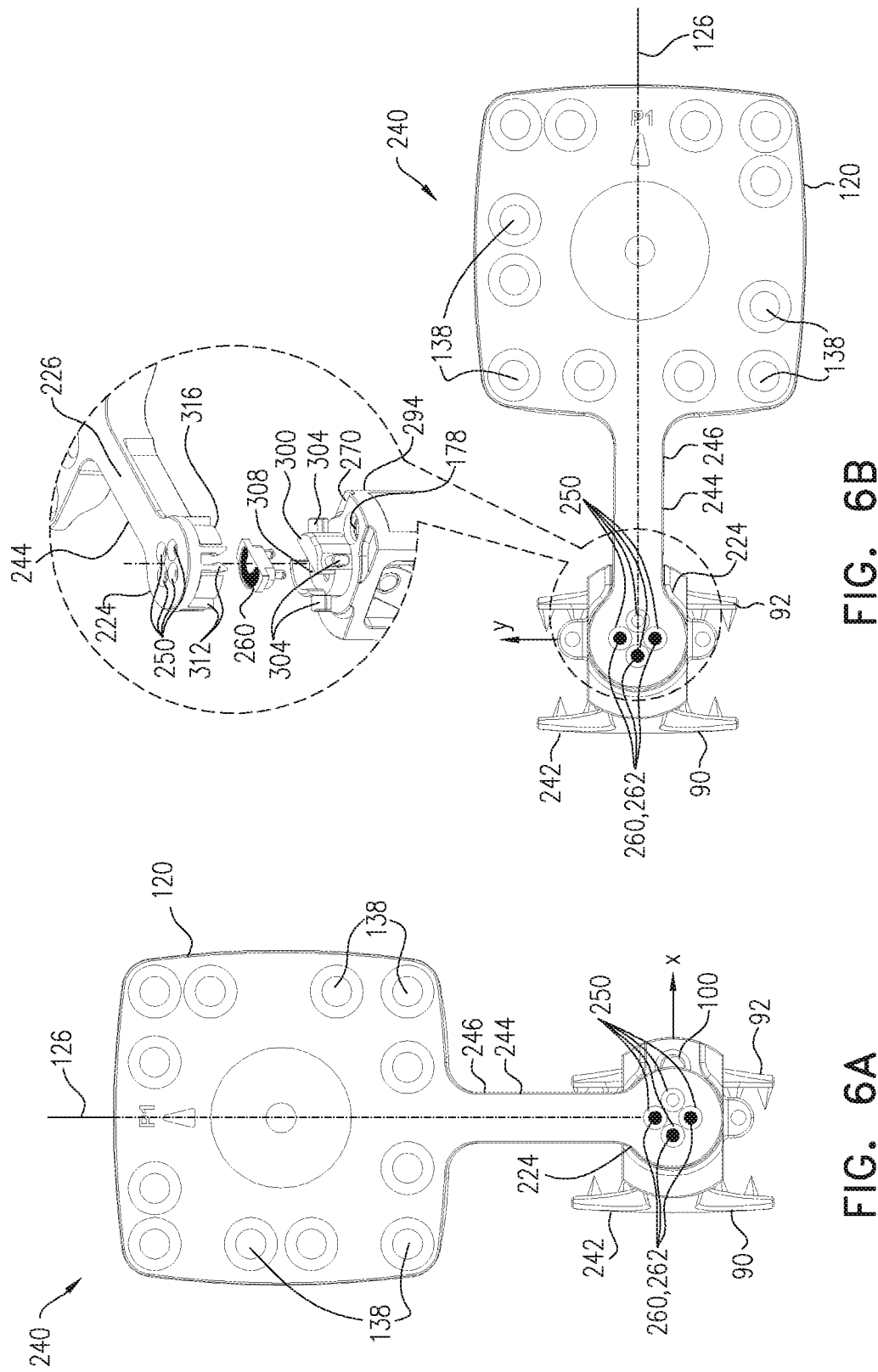

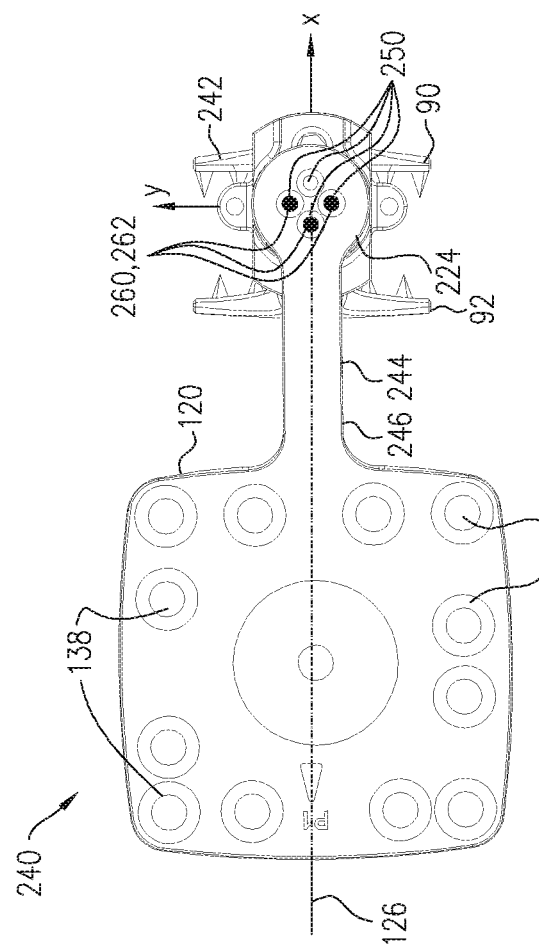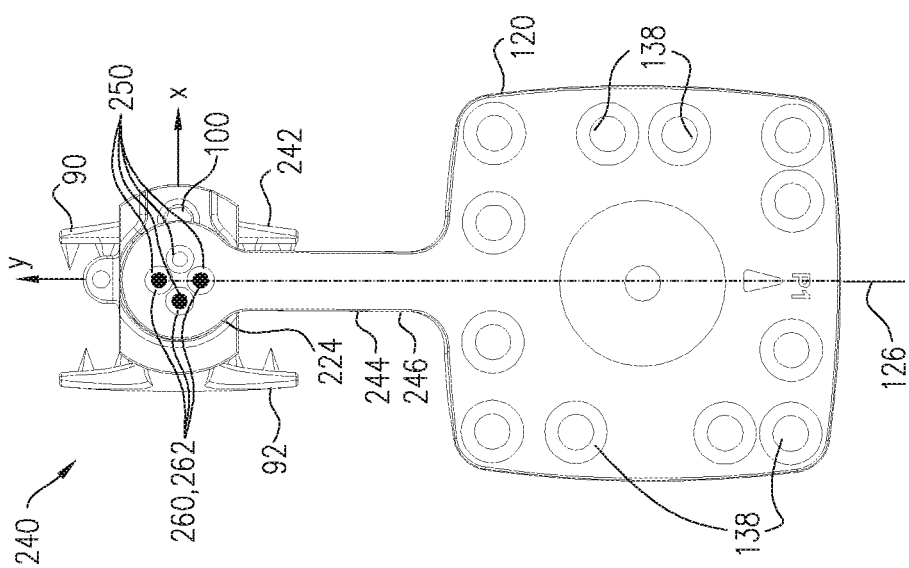

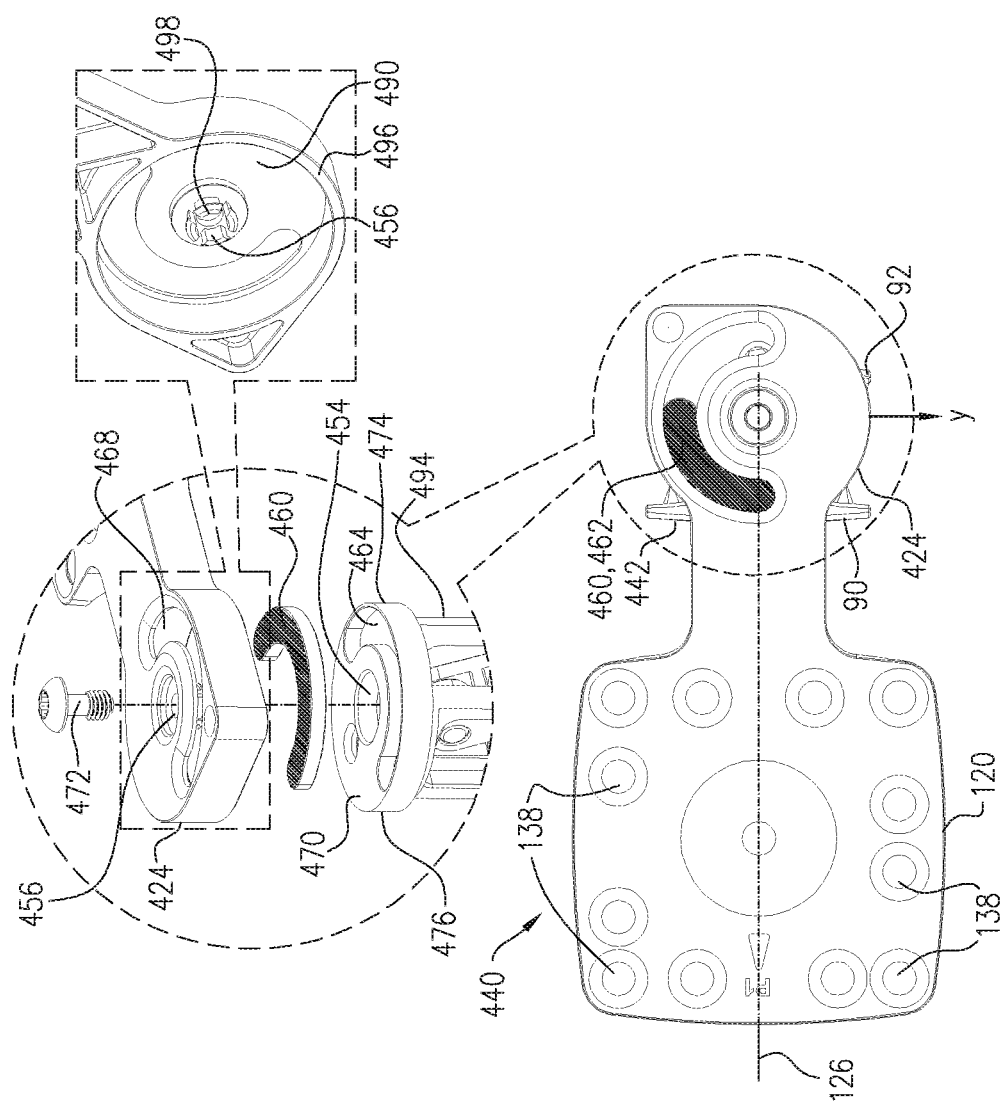
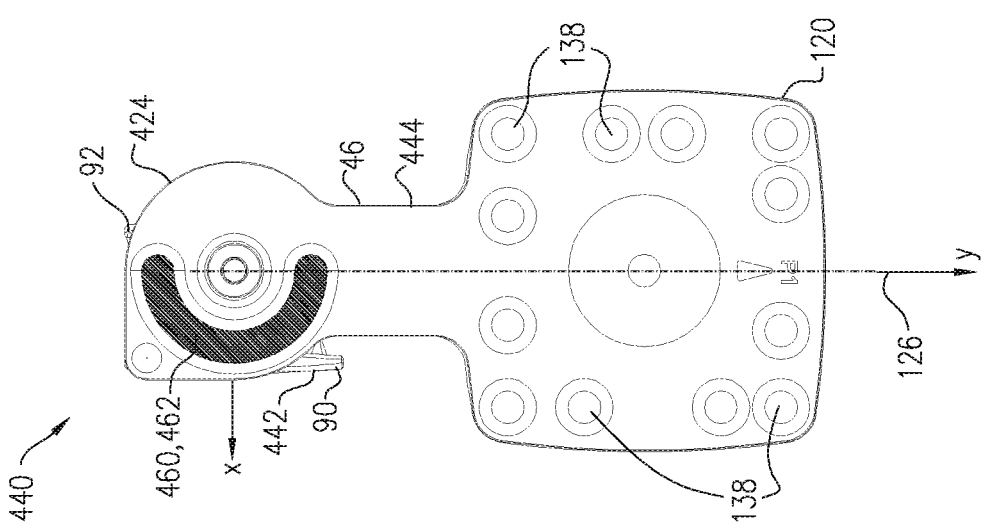
FIG. 7B
FIG. 7A

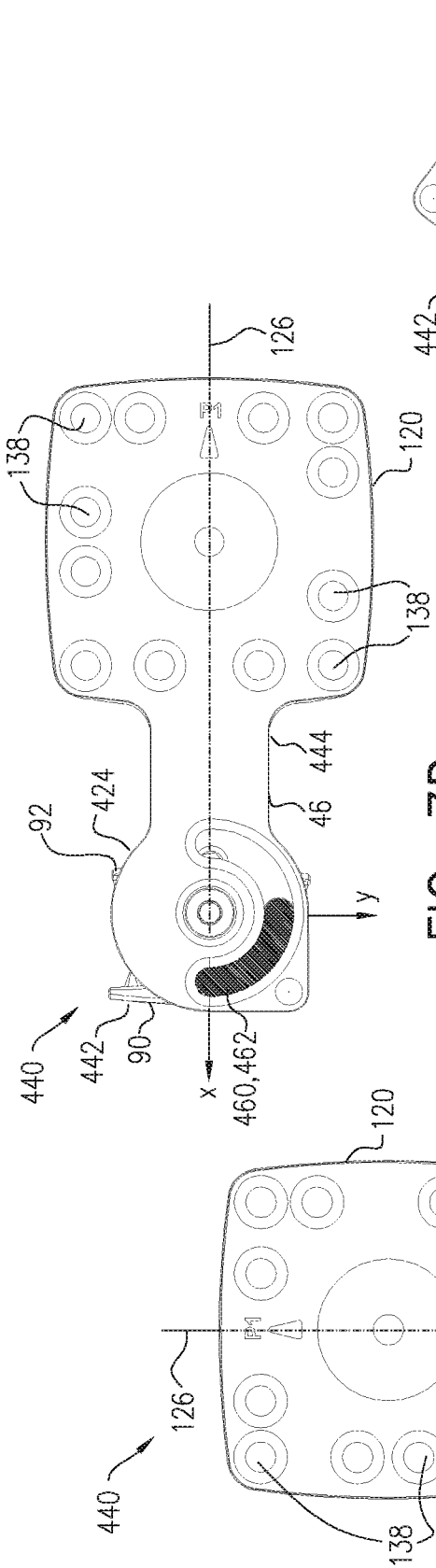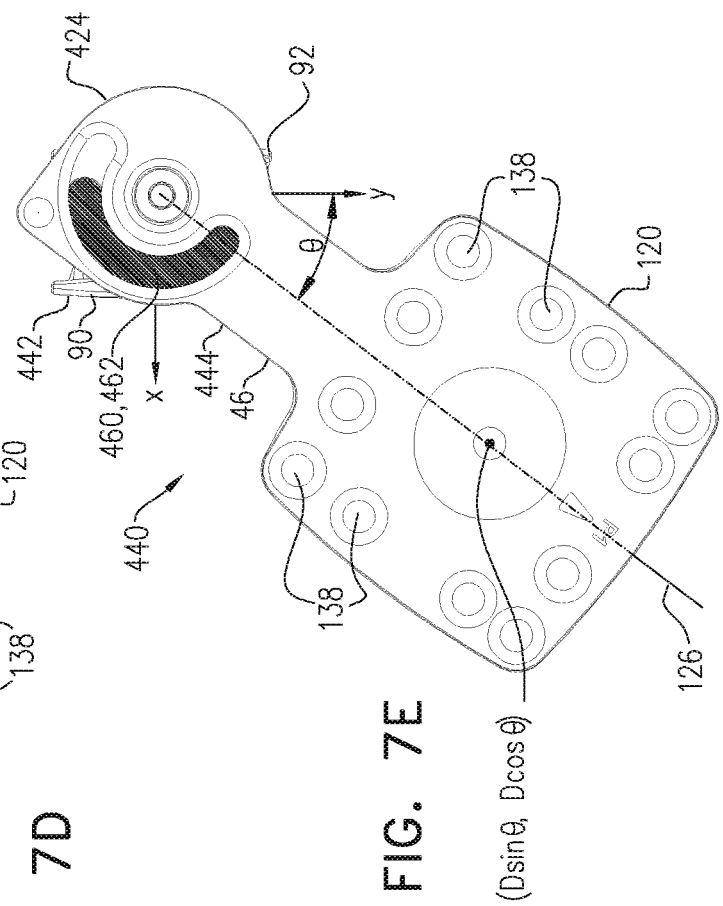
FIG. 7C
FIG. 7D
FIG. 7E

ROTATING MARKER FOR IMAGE GUIDED SURGERY

FIELD OF THE INVENTION

The present invention relates generally to surgery, and specifically to surgery performed using augmented reality.

BACKGROUND OF THE INVENTION

In an augmented reality system used by a physician performing surgery, it is typically necessary to register a frame of reference of a patient with a frame of reference of the augmented reality system used by the physician. Methods for registration are known in the art.

U.S. Pat. No. 8,848,977 to Bammer et al., describes a method for optical pose detection. A self-encoded marker where each feature on the pattern is augmented with a 2-D barcode is provided.

U.S. Pat. No. 9,220,573 to Kendrick et al., describes a system for tracking a tracking device for use with a surgical navigation system. The system can include at least one tracking device having a plurality of faces, and the faces can be operable to generate a signal upon activation.

U.S. Pat. No. 9,378,558 to Kajiwara et al., describes a self-position/self-orientation calculation unit calculating self-position and/or self-orientation in a predetermined coordinate system based on a marker in acquired imaged image data when it is determined that the marker exists within a predetermined area.

U.S. Pat. No. 9,495,585 to Bicer et al., describes methods to find one to one mapping between fiducial markers on a tracked object and fiducial marker projections on an image plane captured by a camera in optical object tracking systems.

U.S. Pat. No. 9,943,374 to Merritt et al., describes an image guidance system for tracking a surgical instrument during a surgical procedure. The image guidance system includes a plurality of cameras adapted to be located external to a surgical area for capturing images of optically visible patterns.

U.S. Pat. No. 10,022,104 to Sell et al., describes a marker that includes a first marker component having a first hydrogen proton density and a first mass density; and a second marker component having a second hydrogen proton density different than the first hydrogen proton density.

U.S. Pat. No. 10,080,616 to Wilkinson et al., describes a system which generates a three-dimensional representation of a bone and reference markers, defines a coordinate system for the three-dimensional representation, and determines locations of the reference markers relative to the coordinate system.

U.S. Pat. No. 10,108,833 to Hong et al., describes a marker with a pattern formed thereon, and which includes an optical system. At least a part of the pattern that uniquely appears depending on a direction in which the pattern is viewed from outside of the marker, through the optical system, is visually identified from the outside of the marker.

U.S. Pat. No. 10,251,724 to McLachlin et al., describes a reference tie that may be secured around a portion of a spine during a surgical procedure and that may be tracked by a surgical navigation system.

U.S. Pat. No. 10,296,805 to Yang et al., describes a marker wherein at least one of a position and pose with respect to a capturing unit is estimated.

U.S. Pat. No. 10,420,626 to Tokuda et al., describes methods for automated detection and registration of medical images using fiducial markers and processing algorithms.

U.S. Pat. No. 10,463,434 to Siegler et al., describes tracking marker support structures that include one or more fiducial reference markers, where the tracking marker support structures are configured to be removably and securely attached to a skeletal region of a patient.

U.S. Pat. No. 10,504,231 to Fiala describes fiducial markers that are printed patterns detected by algorithms in imagery from image sensors for applications such as automated processes and augmented reality graphics.

U.S. Pat. No. 10,537,395 to Perez describes a kinematic connector assembly for kinematically coupling two objects. The kinematic connector assembly comprises a receiver defining a cavity and having a plurality of constraint surfaces accessible in the cavity.

U.S. Patent Application 2003/0210812 to Khamene et al., describes an apparatus for pose determination using single camera tracking in a workspace The apparatus includes a computer programmed for making the pose determination and a tracker camera coupled to the computer for providing a tracking image and for which calibration information is stored.

U.S. Patent Application 2011/0098553 to Robbins et al., describes automatic registration of a magnetic resonance (MR) image that is carried out in an image guidance system by placing MR visible markers at known positions relative to markers visible in a camera tracking system.

U.S. Patent Application 2013/0106833 to Fun describes an input device for providing three-dimensional, six-degrees-of-freedom data input to a computer. The device includes a tracker having tracking points. One array of tracking points defines a first axis. Another array defines a second axis or plane orthogonal to the first axis.

U.S. Patent Application 2015/0150641 to Daon et al., describes a three-dimensional position and orientation tracking system that comprises one or more pattern tags, each comprising a plurality of contrasting portions, and a tracker for obtaining image information about the pattern tags.

U.S. Patent Application 2016/0324583 to Kheradpir et al., describes a patient reference device that includes a housing having a back side and a front side, and at least three tracking markers attached to the front side of the housing. The housing extends around the at least three tracking markers and beyond a horizontal plane defined by tops of the at least three tracking markers.

U.S. Patent Application 20170239015 to Sela et al., describes an apparatus that is at least partially visible by both a three dimensional (3D) scanner system of a medical navigation system and a tracking system of the medical navigation system.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a marker for image guided surgery, including:

a base, having a base axis, connecting to a clamp; and an alignment target, including:

a target region having an alignment pattern formed thereon;

a socket connected to the target region and configured to fit rotatably to the base, whereby the alignment target is rotatable about the base axis; and an optical indicator for the socket indicating an angle of orientation of the alignment target about the base axis.

In a disclosed embodiment the socket is configured to only fit to the base in a plurality of at least two discrete orientations about the base axis. Typically, the plurality of discrete configurations is distributed symmetrically about the base axis. The plurality may consist of four discrete orientations.

In a further disclosed embodiment the socket consists of a plurality of apertures equal to the plurality of discrete orientations, and the optical indicator is configured to be visible through one of the apertures indicative of one of the discrete orientations.

In a yet further disclosed embodiment the socket consists of a plurality of apertures equal to the plurality of discrete orientations, and the optical indicator is configured to be visible through apertures selected and arranged so as to provide an unambiguous identification of each of the discrete orientations.

In an alternative embodiment the socket is configured to fit to the base in a plurality of non-discrete orientations about the base axis. The socket may include an aperture, and the optical indicator may be congruent with the aperture, and a fraction of the optical indicator visible through the aperture may be indicative of one of the non-discrete orientations. The aperture may consist of a semicircular arc.

In a further alternative embodiment the socket is at a fixed distance from the target region, and the marker further includes:

an augmented reality system operative during surgery on a patient; and a processor configured to:

track the alignment target during the surgery, provide a patient tracking vector to the augmented reality system in response to the tracking of the alignment target, calculate a change in the angle of orientation of the alignment target in response to changes in images of the optical indicator, and add a change-of-orientation vector, based only on the fixed distance and the change in the angle of orientation, to the patient tracking vector so as to update the patient tracking vector.

An embodiment of the present invention also provides a method for enabling rotation of a marker during surgery without requiring re-registration, including:

connecting a base, having a base axis, to a clamp;

forming an alignment pattern on a target region of an alignment target;

connecting a socket to the target region, the socket being at a fixed distance from the target region and being configured to fit rotatably to the base, whereby the alignment target is rotatable about the base axis;

providing an optical indicator for the socket indicating an angle of orientation of the alignment target about the base axis;

operating an augmented reality system during the surgery on a patient;

tracking the alignment target during the surgery;

providing a patient tracking vector to the augmented reality system in response to the tracking of the alignment target;

calculating a change in the angle of orientation of the alignment target in response to changes in images of the optical indicator; and adding a change-of-orientation vector, based only on the fixed distance and the change in the angle of orientation, to the patient tracking vector so as to update the patient tracking vector.

The present disclosure will be more fully understood from the following detailed description of the embodiments thereof, taken together with the drawings, in which:

BRIEF DESCRIPTION OF THE DRAWINGS

FIGS. 6A-6D are schematic views of different orientations of an alternative patient marker, according to an embodiment of the present invention;

FIGS. 7A-7E are schematic views of different orientations of another alternative patient marker, according to an embodiment of the present invention;

DETAILED DESCRIPTION OF EMBODIMENTS

Overview

Figure 1:
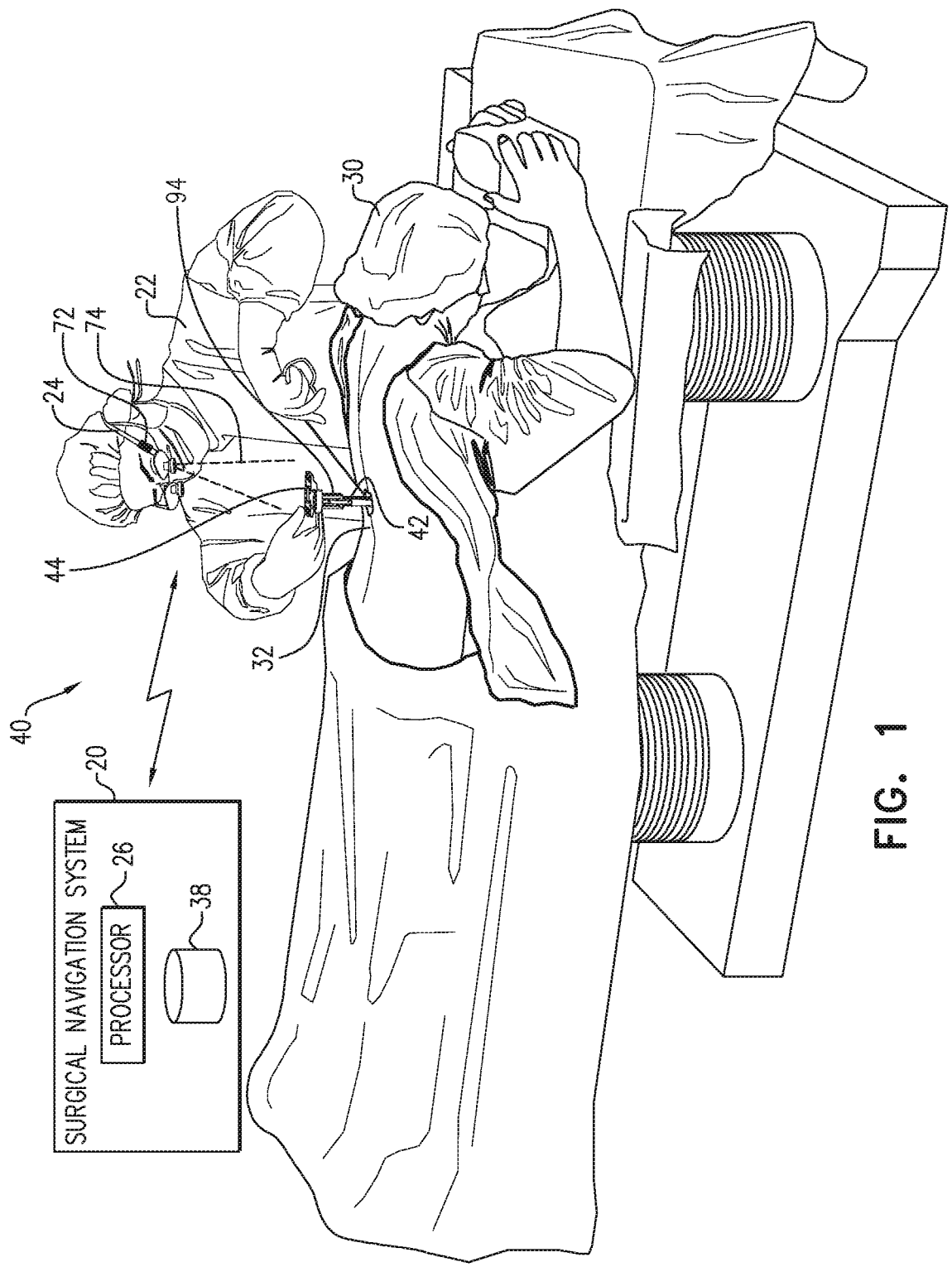
FIG. 1, which is a schematic illustration of a medical procedure, according to an embodiment of the present invention.

In an augmented reality system that is used during surgery on a patient it is necessary to track the movement of the patient. The system typically comprises a head-mounted display worn by a professional performing the surgery, and the tracking is required so as to maintain registration of images of the patient that are presented in the display with the professional's view of the patient.

To track the patient's movement relative to the display, an alignment target may be fixed to the patient and a processor may be configured to track the target. In embodiments of the invention the target is fixed to a base of a clamp that is clamped to a bone of the patient, so that the target, when attached to the clamp base, acts as a patient marker. If the surgery is on the spine of the patient, the bone may comprise one or more spinous processes of the patient's vertebrae.

The professional typically registers the tracked location of the target of the patient marker with the patient, and this registration is used by the processor. So long as the registration is valid, tracking of the target allows the processor to compensate for relative movement of the patient.

However, during the procedure the alignment target may interfere with the surgery being performed, for example, by obstructing the professional's view and/or by restricting the professional's action. In this case, in prior art systems, the alignment target may be re-oriented with respect to the clamp, to overcome the interference. The re-orientation, typically detaching the target from the clamp, then re-attaching the target to the clamp, necessitates re-registration by the professional of the target with the clamp.

Embodiments of the present invention allow for re-orientation of the target without the necessity of re-registration by the professional. The alignment target comprises a target region having an alignment pattern formed thereon. A socket comprised in the alignment target is fixedly connected at a known distance to the target region, and the socket is configured to fit rotatably to the base of the clamp, so that the alignment target is rotatable about a base axis defined by the clamp base. The alignment target also comprises an optical indicator for the socket indicating an angle of orientation of the alignment target about the base axis.

During the procedure the processor operating the augmented reality system may track the alignment target so as to provide a patient tracking vector to the system, the vector maintaining the registration referred to above. The processor may then calculate a change in the angle of orientation of the alignment target in response to changes in images of the optical indicator. Based only on the change in the angle of orientation and the known target region—socket distance, the processor may calculate a change-of-orientation vector, and then add this vector to the patient tracking vector so as to update the patient tracking vector.

The updated patient tracking vector acts to automatically re-register the tracking of the alignment target, so that no re-registration by the professional is necessary.

System Description

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Reference is now made to FIG. 1, which is a schematic illustration of a medical procedure, according to an embodiment of the present invention. During the procedure, performed by a professional 22, the professional uses a surgical navigation system 20, which assists the professional in performance of the procedure. Surgical navigation system 20 comprises a processor 26, which operates elements of the system, and which communicates with an augmented reality assembly 24, worn by professional 22, that is incorporated in the system. While assembly 24 may be incorporated for wearing into a number of different retaining structures on professional 22, in the present description the retaining structure is assumed to be similar to a pair of spectacles. Those having ordinary skill in the augmented reality art will be aware of other possible structures, such as incorporation of the augmented reality assembly into a head-up display that is integrated into a helmet worn by the user of system 20, and all such structures are assumed to be comprised within the scope of the present invention.

In one embodiment processor 26 is assumed to be incorporated within a stand-alone computer, and the processor typically communicates with other elements of the system, including assembly 24, wirelessly, as is illustrated in FIG. 1. Alternatively or additionally, processor 26 may use optical and/or conducting cables for the communication. In further alternative embodiments processor 26 is integrated within assembly 24, or in the mounting of the assembly. Processor 26 is typically able to access a database 38, wherein are stored images and other visual elements used by system 20. Software enabling processor 26 to operate system 20 may be downloaded to the processor in electronic form, over a network, for example. Alternatively or additionally, the software may be provided on non-transitory tangible media, such as optical, magnetic, or electronic storage media.

Assembly 24 comprises, inter alia, an image capturing device 72, also termed herein a camera 72, that has a field of view 74 and that is configured to capture images in the visible spectrum. Assembly 24 and functions of system 20, processor 26, and device 72 are described below. An assembly similar to augmented reality assembly 24, and its operation, are described in U.S. Pat. No. 9,928,629, to Benishti, et al., whose disclosure is incorporated herein by reference.

The medical procedure exemplified here is performed on a patient 30, and during an initial stage of the procedure professional 22 makes an incision 32 into the patient's back. The professional then inserts a spinous process clamp 42, into the incision, so that opposing jaws of the clamp are located on opposite sides of a spinous process. The professional adjusts clamp 42 to grip one or more spinous processes, selected by the professional, of the patient.

The professional attaches an alignment target 44 to a base 94 of the clamp, the target when attached to the base operating as a patient marker 40. Patient marker 40 thus comprises alignment target 44 coupled to base 94. As is described below, patient marker 40 is used by system 20 to determine the position and orientation of patient 30 during the medical procedure.

Figure 2:
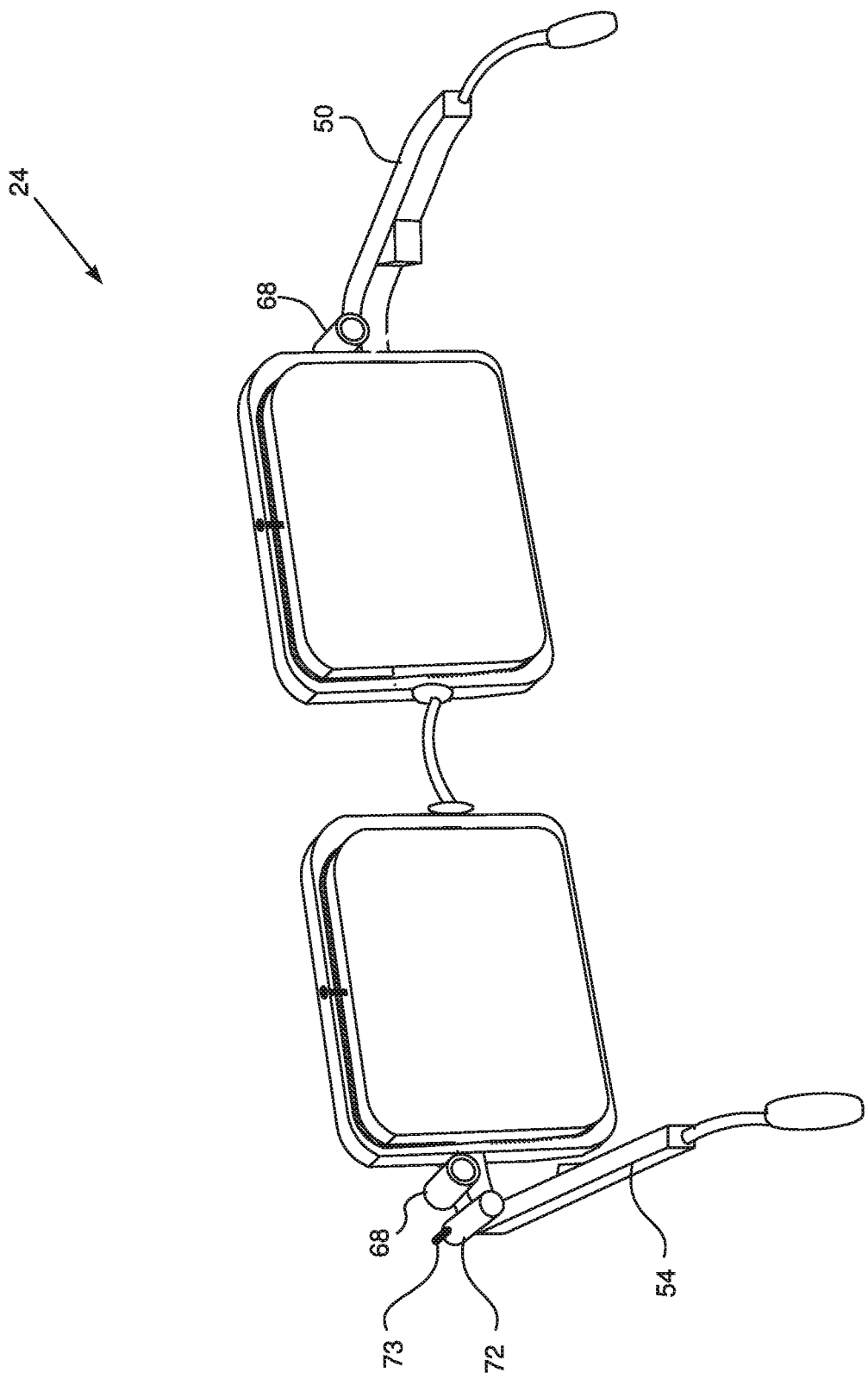
FIG. 2 is a schematic diagram illustrating an augmented reality assembly used in the procedure, according to an embodiment of the present invention.

FIG. 2 is a schematic diagram illustrating assembly 24, according to an embodiment of the present invention. As stated above, assembly 24 is configured, by way of example, as a pair of spectacles 50 mounted on a frame 54.

At least one image capturing device 68 is attached to frame 54. Typically, devices 68 comprise cameras configured to capture images of scenes viewed by the professional's eyes, including images of marker 40 in the visible spectrum.

As stated above assembly 24 also comprises camera 72, which is configured to capture images of elements of a scene, including marker 40, in front of assembly 24. The images are produced from radiation projected by a projector 73 that is in the spectrum detected by camera 72. Projector 73 is located in close proximity to camera 72, so that radiation from the projector, that has been retroreflected, is captured by camera 72. The camera typically has a bandpass filter configured to block other radiation, such as that projected by surgical lighting. Typically, camera 72 and projector 73 operate in a non-visible region of the spectrum, such as in the near infra-red spectrum. As is described below, at least some retroreflected radiation is typically received from marker 40, and processor 26 uses the image of the marker produced by camera 72 from the received radiation to track the marker, and thus the position and orientation of patient 30. By tracking the position and orientation of patient 30, the processor is able to present, to professional 22 in assembly 24, images of the patient that are correctly registered with the physician's actual view of the patient.

Figure 3:
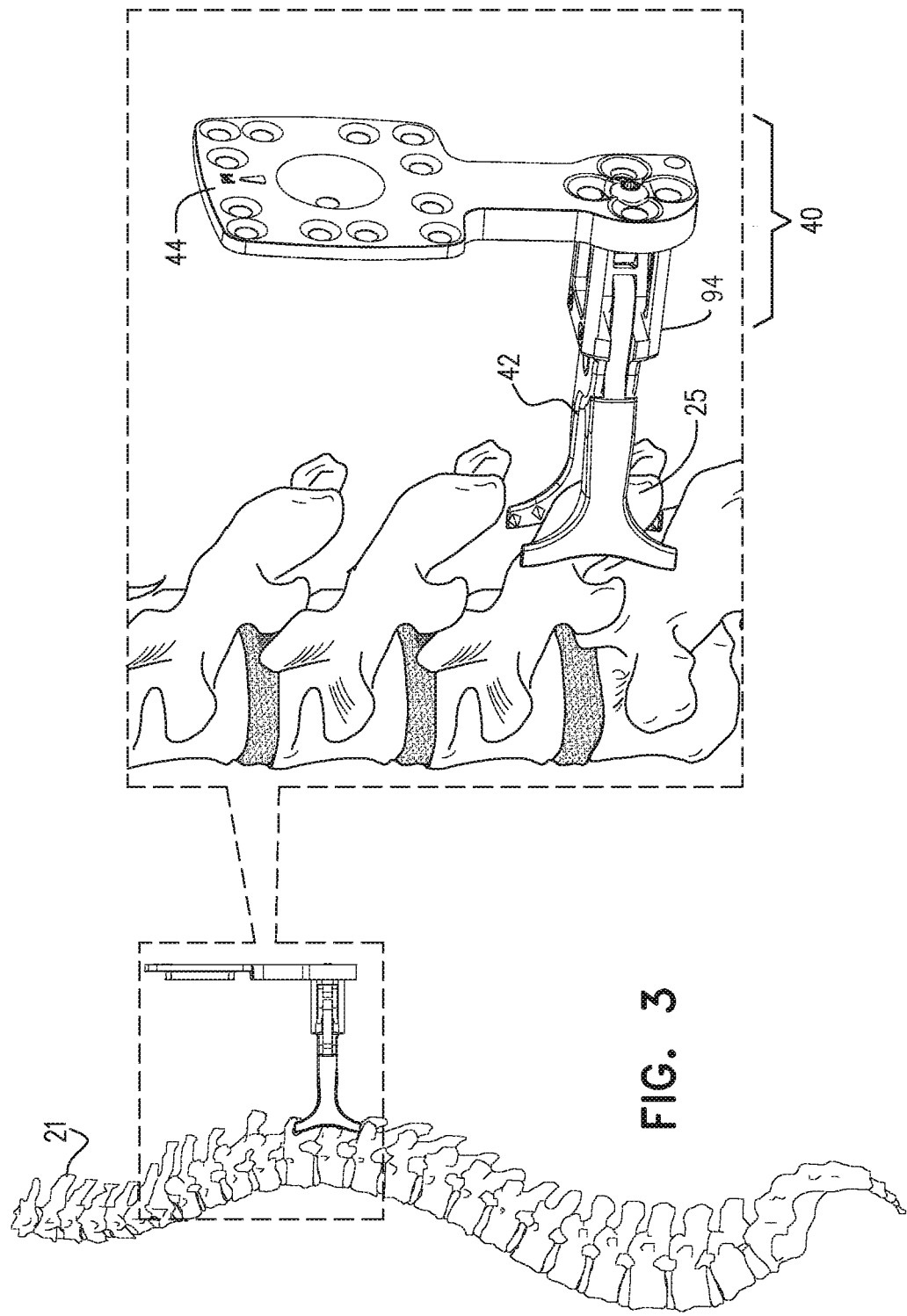
FIG. 3 schematically illustrates the situation after a patient marker has been attached to a clamp which is inserted and adjusted in a patient, according to an embodiment of the present invention.

FIG. 3 schematically illustrates the situation after clamp 42 has been inserted and adjusted in patient 30, according to an embodiment of the present invention. Target 44 is then attached to base 94 of the clamp, forming marker 40. The figure illustrates that clamp 42 has been attached to grip a bone 21 of patient 30, specifically to grip a spinous process 25 of vertebrae of the spine of the patient. After attachment, alignment target 44 is external to the patient. As shown in FIG. 3, clamp 42 comprises teeth, protruding internally from jaws of the clamp, the teeth facilitating the clamp fixedly gripping the spinous processes. Marker 40 is described in more detail below with reference to FIGS. 4A-4E.

Figure 4A:
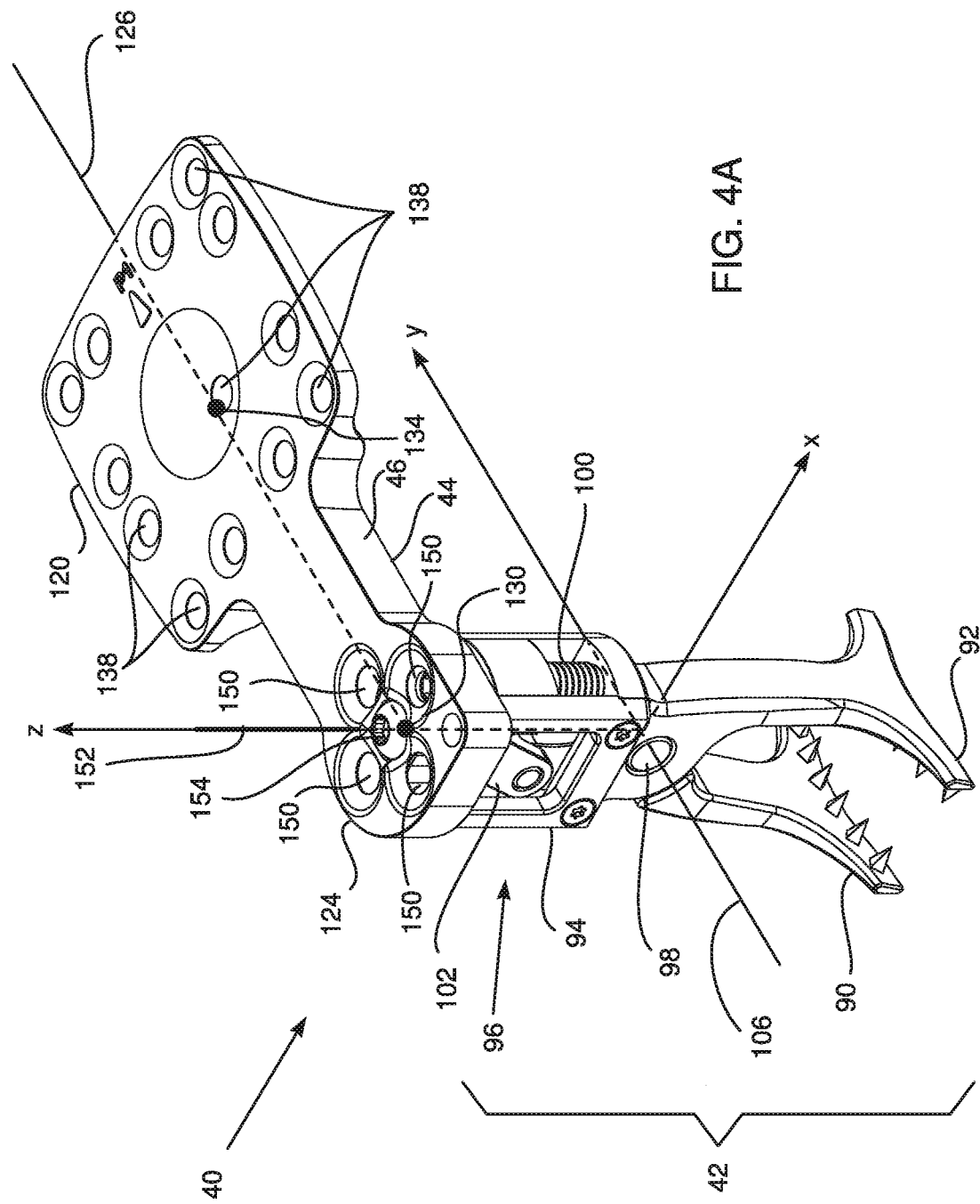
FIG. 4A is a schematic perspective view of the marker.

FIG. 4A is a schematic perspective view of marker 40, and FIGS. 4B-4E are schematic views of different orientations of the marker, according to an embodiment of the present invention. As stated above, marker 40 is formed by attaching alignment target 44 to base 94 of clamp 42. The clamp is described below.

Clamp 42 comprises a pair of jaws 90, 92 in a lower section of the clamp. The jaws are coupled to clamp base 94 in an upper section of the clamp, the base comprising a jaw adjustment mechanism 96. In the embodiment described herein, jaw 92 is fixed to base 94, and jaw 90 moves with respect to jaw 92, by being rotated about a hinge pin 98. Jaw adjustment mechanism 96 comprises an adjustment screw 100, which is coupled by a lever 102 to jaw 90 so that rotation of the screw causes jaw 90 to approach or retreat from jaw 92. Thus professional 22 is able to cause the jaws of clamp 42 to grip or release a bone, such as spinous process 25, by rotating screw 100. Hinge pin 98 defines a hinge axis 106 about which jaw 90 rotates, and each jaw 90, 92 is substantially parallel to the hinge axis.

For clarity, in the description herein, elements of marker 40 are assumed, by way of example, to be referenced to an xyz set of orthogonal axes, with origin at the center of hinge pin 98. The xyz set of axes is illustrated in FIG. 4A, wherein a y-axis is assumed to correspond to hinge axis 106, an x-axis is orthogonal to a plane including jaws 90 and 92, and a z-axis is orthogonal to the x- and y-axes.

Alignment target 44 comprises a target region 120 and a socket 124, the target region and the socket being fixedly connected together by a connecting rod 46. Alignment target 44, together with its components target region 120 and socket 124, are generally planar, herein termed xy planar since they are assumed to be in a plane parallel to the x- and y-axes. Embodiments of the present invention measure an angle of orientation of alignment target 44 to clamp 42, so that a line 126, constructed from a center 130 of the socket to a center 134 of the target region and extended therefrom, is herein assumed to indicate a direction of orientation of the alignment target 44.

Target region 120, by way of example, is approximately rectangular and comprises optical elements 138. Elements 138 are arranged in a three-dimensional (3D) pattern with no rotational axis of symmetry (other than a trivial axis of symmetry for rotating by 360°), and no mirror plane of symmetry, so that an image of the elements enables an unambiguous determination of the location and orientation of the target region. Elements 138 are typically retroreflectors. An entity with an arrangement of optical elements similar to the arrangement herein is described in PCT Patent Application WO2019211741A1, which is incorporated herein by reference.

As stated above, socket 124 is generally planar, and is assumed to define an axis 152 through socket center 130 and orthogonal to an xy plane. In cases where socket center 130 lies on the z-axis, axis 152 is coincident with the z-axis, as is illustrated in FIG. 4A. Socket 124 comprises four substantially similar apertures 150 which are distributed symmetrically about axis 152. Socket 124 comprises a central hole 156, and a screw 154 is configured to penetrate the hole and connect the socket to an upper surface 170 of clamp base 94, as is illustrated in the call-out of FIG. 4C.

Surface 170 is xy planar, being parallel to an xy plane, and comprises four protrusions 174 distributed symmetrically about the z-axis. There is an aperture 178 in the surface providing access to adjustment screw 100, and the positions of apertures 150 are selected so that regardless of the orientation of target 44, access to screw 100 is available through one of apertures 150. There is also a shaped indentation 182, comprising an arc 186, in surface 170, the indentation being shaped to accept a colored insert 160.

Figures 4B, 4C:
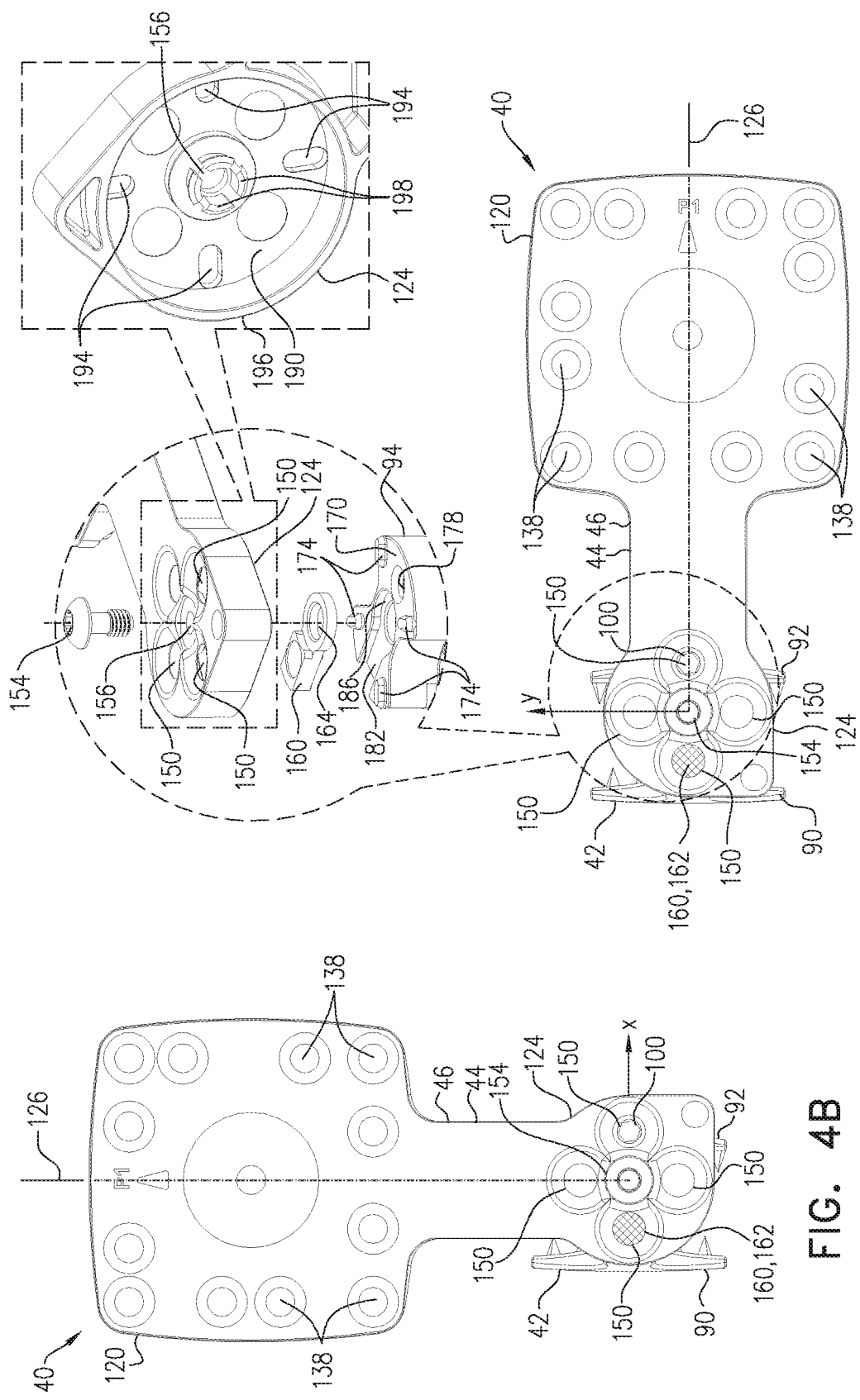
FIGS. 4B-4E are schematic views of different orientations of the marker, according to an embodiment of the present invention.
Figure 4E:
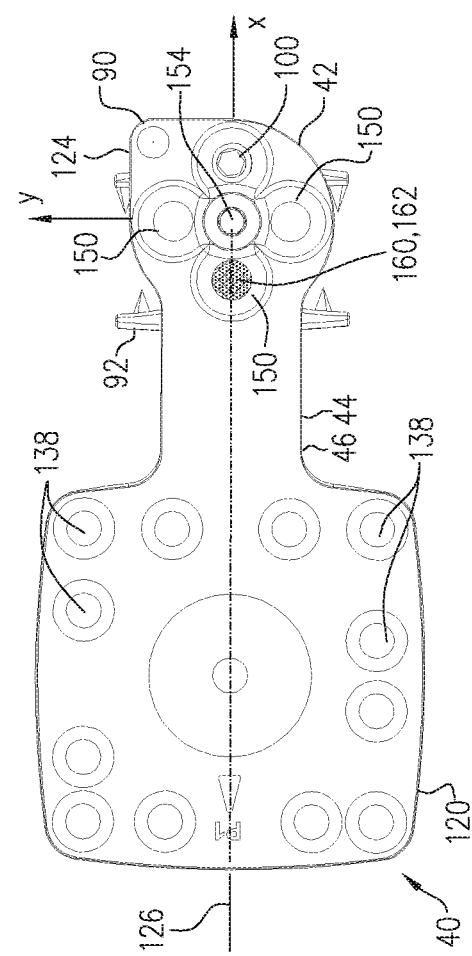
Figure 4D:
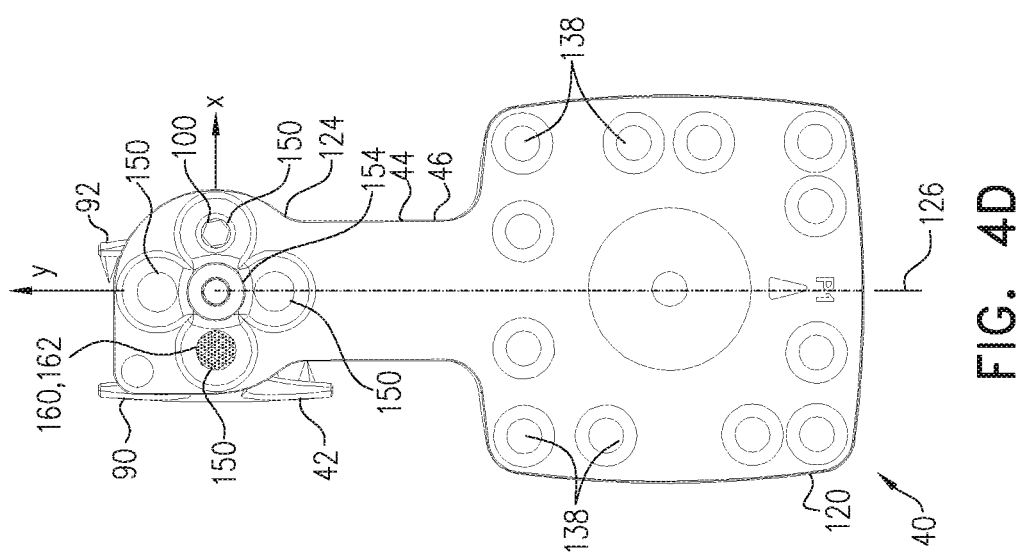

As is also illustrated in FIG. 4C, socket 124 comprises a planar lower surface 190, within which are inset four indents 194, distributed symmetrically about socket central hole 156, and configured to mate with protrusions 174. Surface 190 is surrounded by a circular wall 196. Extending from surface 190 are a plurality of arcs 198, also distributed symmetrically about socket central hole 156, and configured to mate with arc 186 of indentation 182.

FIGS. 4B-4E illustrate the four different discrete orientations that alignment target 44 is able to make with clamp 42, when the target is connected to the clamp with screw 154 so that socket 124 mates with base 94. Assuming that the positive y-axis of the clamp corresponds to an orientation of 0°, and that orientations are measured as clockwise rotations about the z-axis from the y-axis, FIGS. 4B, 4C, 4D, and 4E correspond respectively to the target having discrete orientations of 0°, 90°, 180°, and 270°. At each orientation arcs 198 mate with arc 186, protrusions 174 mate with indents 194, and wall 196 mates with outer circular edges of base 94, the mating ensuring that socket 124 is centered with respect to the z-axis.

As is illustrated in FIGS. 4B-4E, at each orientation insert 160 is visible through one of apertures 150, and the visible insert acts as an optical indicator 162 of the orientation. During operation of system 20, processor 26 calculates coordinates of a directed line segment between indicator 162 and center 134, the coordinates acting as an orientation metric. For each orientation there is a unique directed line segment, i.e., a unique orientation metric, so that processor 26 is able to use the calculated coordinates as an orientation indicator.

Table I below shows coordinates, the orientation metric, of the directed line segment for each of the four orientations of target 44. (For clarity, Table I, and Table II below, are drawn to a two-dimensional system, and may be adapted, mutatis mutandis, to a three-dimensional or higher system.) The coordinates are calculated assuming that indicator 162 lies on a circle radius r centered at center 130 of socket 120, and that there is a separation of D between center 130 and center 134.

TABLE I

| Orientation | Orientation Indicator Orientation Metric |
|---|---|
| 0° | (−r, 0) − (0, D) = (−r, −D) |
| 90° | (−r, 0) − (D, 0) = (−r − D, 0) |
| 180° | (−r, 0) − (0, −D) = (−r, D) |
| 270° | (−r, 0) − (−D, 0) = (D − r, 0) |

As is described herein, marker 40 is used to track the location of patient 30, typically the patient's bone, with respect to assembly 24, by tracking the location of target region 120. Since the location of the target region is fixed with respect to the patient's bone to which marker 40 is clamped, because the marker is inflexible, tracking of the patient's bone may be accomplished by tracking of the target region, and adding a fixed adjustment vector due to the differing physical positions of the target region and the bone.

Furthermore, since the target region positions have a one-to-one correlation with the orientations, and since the different target region positions are in known geometric relations to each other, these geometric relations may be pre-programmed as change-of-orientation vectors and used to continue tracking the patient when the target region orientation is changed.

For example, if target region 120 is a distance D from socket 124, then the target region positions for the orientations 0°, 90°, 180°, and 2700 (illustrated in FIGS. 4B, 4C, 4D, and 4E) may be respectively represented by the two-dimensional ordered pairs (0, D), (D, 0), (0, −D), and (−D, 0). If an initial target region is in the 0° orientation, then the geometric relations, i.e., the change-of-orientation vectors, to the other three orientations are as given in Table II:

TABLE II

| New Orientation | Change-of-orientation Vector (From 0° Orientation) |
| --- | --- |
| 90° | (D, 0) − (0, D) = (D, −D) |
| 180° | (0, − D) − (0, D) = (0, −2D) |
| 270° | (− D, 0) − (0, D) = (−D, −D) |

It will be understood that the three change-of-orientation vectors presented in Table II do not vary with movement of marker 40. The vectors depend only on the initial and final orientation of the target region, and so, as stated above, may be pre-programmed. It will also be understood that sets of three change-of-orientation vectors from the other possible initial orientations (90°, 180°, and 270°) may be calculated as for Table II, and may also be pre-programmed.

As is explained further below, in embodiments of the present invention, when the target region orientation changes a processor adds an appropriate change-of-orientation vector to an initial tracking vector of a patient marker. This enables continuous tracking of a patient by the marker without re-registration of the marker.

Figure 5:
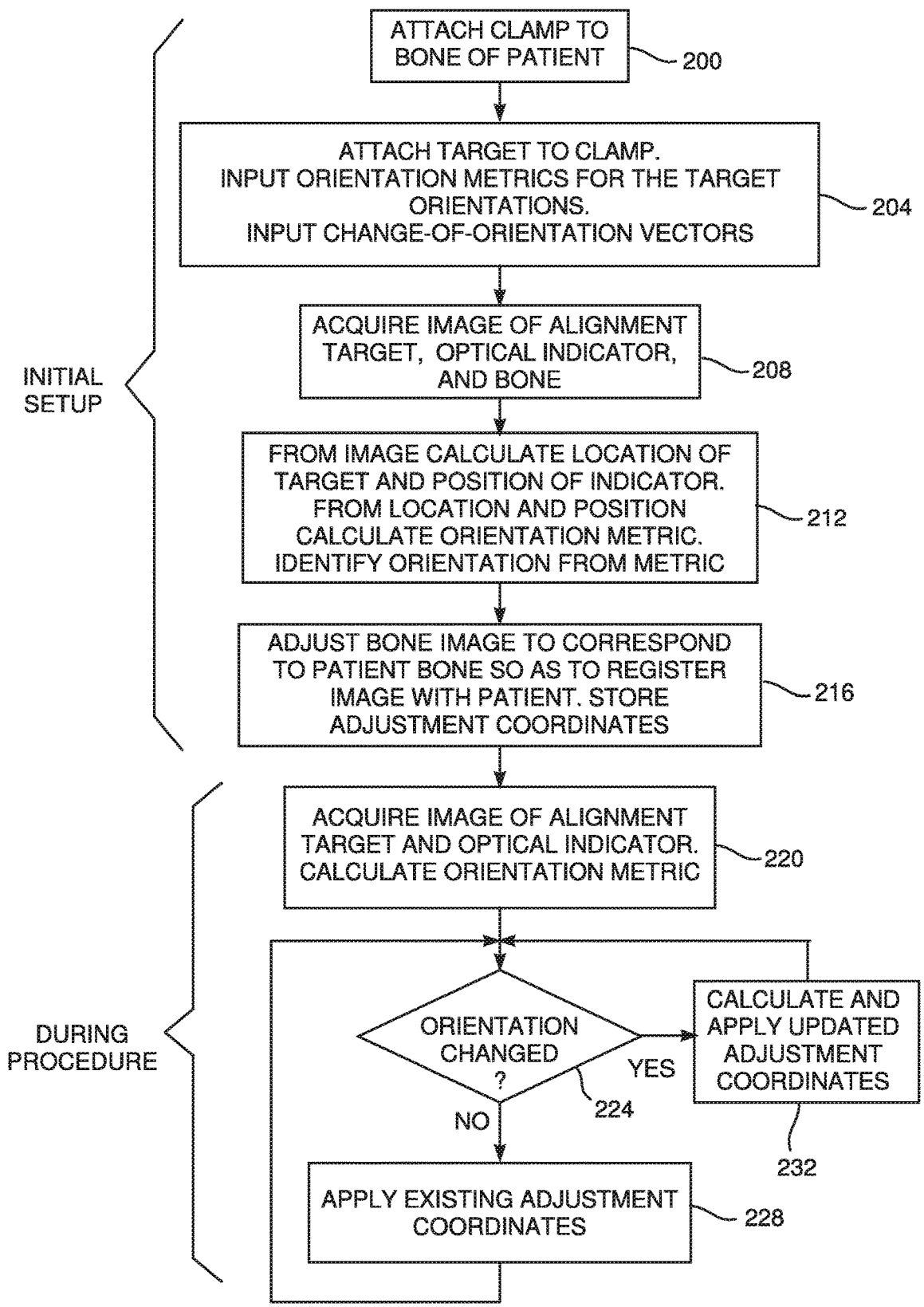
FIG. 5 is a flowchart describing the use of the marker in the medical procedure, according to an embodiment of the present invention.

FIG. 5 is a flowchart describing the use of marker 40 in the medical procedure referred to above, according to an embodiment of the present invention.

In an initial step 200, professional 22 attaches clamp 42 to a bone of patient 30, herein assumed to comprise spinous process 25 of the patient, by rotating screw 100.

In a target attachment step 204, the professional attaches alignment target 44 to the clamp, by aligning socket 124 with surface 170 of clamp base 94, and screwing screw 154. It will be understood that the attached orientation is one of the four orientations illustrated in FIGS. 4B-4E, so that after the attachment, insert 160 is visible through one of apertures 150, and acts as optical indicator 162.

The values of r and D, and the sets of orientation metrics for the orientations of the target, described above with reference to Table I, are input to processor 26. In addition, the sets of change-of-orientation vectors coordinates, described above with reference to Table II, are also input to the processor.

In an image acquisition step 208, processor 26 acquires, using camera 72 and/or one or more devices 68, an image of optical elements 138 of target region 120, of indicator 162, and of the bone of patient 30, or of a region close to the bone, such as incision 32.

In an analysis step 212, the processor analyzes the acquired image to find a location, comprising an orientation and a position, of target region 120. The position of target region is herein, by way of example, assumed to correspond to center 134. Once the target region location has been found, the processor initiates tracking of the target region.

The processor also finds a position of indicator 162. From coordinates of the two positions the processor calculates coordinates of an orientation metric (as in Table I) joining the positions, and from the metrics stored in step 204, identifies the orientation of step 204.

In an adjustment step 216, the processor presents the image of the bone or of the region close to the bone, acquired in step 208, to professional 22 in augmented reality assembly 24. The professional adjusts coordinates of the presented image to correspond with the actual image visible to the professional through the assembly, and the processor stores the adjustment coordinates. The processor then applies the stored adjustment coordinates as an adjustment vector, together with the tracking of the tracked region (initiated in step 212), to the presented image, so as to register the presented image with patient 30 on a continuing basis.

The processor continues to apply the stored adjustment vector, which acts a patient tracking vector, as long as the orientation of step 204 is unchanged. It will be understood that the registration using the stored adjustment vector counteracts any relative movement between the patient and assembly 24.

Steps 200-216 correspond to an initial setup of navigation system 20. Steps 220-232, described below, correspond to steps of the flowchart that may be implemented during the medical procedure for which system 20 is used.

In a continuing imaging step 220, the processor, in addition to acquiring an image of patient 30, acquires an image of target 44, including target region 120 and indicator 162. From the images of region 120 and indicator 162, the processor calculates an orientation metric.

In a decision step 224 the processor checks if the metric calculated in step 220 is different from that calculated in step 212, so as to check if the target region has changed orientation. If the decision returns negative, i.e., there is no change in orientation, then in a continuation step 228 the processor continues to use the existing adjustment coordinates, i.e., those of step 216.

If the decision returns positive, i.e., there is a change in orientation, then in an update step 232 the processor calculates updated adjustment coordinates, by adding the appropriate change-of-orientation vector, from step 204, to the existing adjustment coordinates. The processor applies the updated coordinates in presenting the image of the bone, or of the region close to the bone, to professional 22 in augmented reality assembly 24.

It will be understood that a positive return of decision 224 is typically caused by professional 22 changing the orientation of target 44. The professional changes the orientation by unscrewing screw 154, realigning socket 124 on surface 170 so that target 44 is in a new orientation, then screwing screw 154 to fix the target in its new orientation. In some embodiments the professional may pause processor 26 tracking target 44 while positioning target 44 in its new orientation.

The professional typically repositions target 44 to improve access to, and/or to improve visibility to, part of the patient. It will be understood that there is no need to repeat steps 200-220 after the repositioning, since the new adjustment coordinates can be calculated from the known geometric relations of the two orientations of target 44. (It will also be understood that regardless of any repositioning, adjustment screw 100 is always accessible via one of apertures 150, since the screw aligns with the apertures.)

From steps 228 and 232 control returns to decision step 224, so that during the procedure the processor applies steps 224-232 iteratively.

FIGS. 6A-6D are schematic views of different orientations of a patient marker 240, according to an embodiment of the present invention. Marker 240 comprises a clamp base 294 which is coupled to an alignment target 244. Clamp base 294 is the base of a clamp 242. Apart from the differences described below, the operation of marker 240, clamp 242, base 294, and target 244 is generally similar to that of marker 40, clamp 42, base 94, and target 44, and elements indicated by the same reference numerals in both markers are generally similar in construction and in operation. As for marker 40, target 244 has four different discrete orientations with respect to clamp 242. The axes for marker 240 are as for marker 40.

In contrast to upper surface 170 of clamp base 94 of clamp 42, an upper xy surface 270 of clamp base 294 of clamp 242 is surmounted by a circular turret 300. Fixed to turret 300 are four protuberances 304, distributed symmetrically about a center of the turret, and lying in an xy plane, parallel to surface 270. Turret 300 comprises a recess 308, which is configured to accept an insert 260 that typically is colored.

As for socket 124, a socket 224 of target 244 comprises four apertures 250 distributed symmetrically about a center of the socket. However, socket 224 is smaller than socket 124, and regardless of target orientation, an aperture 250 does not align with screw 100. Rather, socket 224 is small enough so that in at least some target orientations, e.g. those of FIGS. 6A, 6C and 6D, screw 100 is accessible from outside the socket.

A connecting rod 246 connects target 120 to socket 224, but typically has a smaller width than rod 46.

Socket 224 has a lower circular wall 316 which has an internal surface which is configured to mate with turret 300. Set within the wall are four clips 312 which are distributed symmetrically about a center of the socket, and which are positioned to mate with protuberances 304. When clips 312 mate with protuberances 304, they hold socket 224 so that wall 316 surrounds and contacts an outer surface of turret 300, and so the socket is fixed to the turret.

Because protuberances 304 and mating clips 312 are distributed symmetrically, it will be understood that target 244 can mate with clamp 242 in one of four orientations illustrated in FIGS. 6A-6D, and that in each orientation a center of socket 224 aligns with a center of turret 300.

Unlike marker 40, where optical indicator 162 is formed from the visibility of insert 160 through one of apertures 150, in marker 240 an optical indicator 262 comprises insert 260 as viewed through three apertures 250, as illustrated in FIGS. 6A-6D.

The description of the flowchart of FIG. 5 applies to marker 240, mutatis mutandis. For example, a position of indicator 262 may be assumed to be the position of the central one of the three apertures 260.

Markers 40 and 240 each have four symmetrically distributed discrete orientations. However, embodiments of the present invention may have other numbers of symmetrically distributed orientations, where the number may be as little as two.

The number of apertures 150 corresponds to the number of discrete orientations. As exemplified by indicator 162 the number of apertures used to generate the optical indicator may be a single aperture. Alternatively, as exemplified by indicator 262, the number of apertures used to generate the optical indicator may comprise any fixed number of apertures that is at least one less than the total number of apertures. In this case the apertures are selected and arranged so that when rotated, they provide an unambiguous identification of each of the discrete orientations.

Thus, for four apertures, corresponding to four discrete orientations, the indicator may be two adjacent apertures, but not two apertures opposite each other, since two apertures opposite each do not provide an unambiguous identification of each orientation.

FIGS. 7A-7E are schematic views of different orientations of a patient marker 440, according to an embodiment of the present invention. Marker 440 comprises a clamp base 494 which is coupled to an alignment target 444. Clamp base 494 is the base of a clamp 242. Apart from the differences described below, the operation of marker 440, clamp 442, base 494, and target 444 is generally similar to that of marker 40, clamp 42, base 94, and target 44, and elements indicated by the same reference numerals in both markers are generally similar in construction and in operation. Unlike marker 40, where target 44 can only make discrete orientations with respect to clamp 42, target 444 in marker 440 can make multiple non-discrete, substantially continuous, orientations varying from 0°-360° with respect to clamp 442.

FIGS. 7A-7E have been drawn on the same set of xyz axes as for marker 40 (although the axes are rotated 180° compared to those of FIGS. 4B-4E), and orientations are measured as clockwise rotations about the z-axis from the y-axis. FIGS. 7A, 7B, 7C, and 7D, correspond respectively to the target having orientations of 0°, 90°, 180°, and 270° relative to the clamp.

FIG. 7E illustrates the target having an orientation of θ relative to the clamp, where 0°≤θ<360°, and coordinates of a center point of the target region have been marked as (D sin θ, D cos θ) where D is the distance of the target region center point from the z-axis.

In contrast to upper surface 170 of clamp base 94 of clamp 42, an upper xy plane surface 470 of an upper plate 476 of clamp base 494 is circular. Surface 470 has a central circular indent 454 symmetrically situated in the surface, and the indent is terminated at its lower end by a female thread. Surface 470 also has an indent 464 which is in the form of a semicircular arc, centered on a center of circular surface 470. An insert 460 that is a semicircular arc and that is typically colored is inserted into indent 464, and the insert is dimensioned so that an upper surface of the insert is level with surface 470.

A socket 424 of target 444 comprises a planar lower surface 490 which is surrounded by a circular wall 496 that is configured to mate with an outer cylindrical surface 474 of plate 476. Extending from surface 490 are a plurality of arcs 498, distributed symmetrically about a socket central hole 456, configured to mate with indent 454. Socket 424 also comprises a semicircular aperture 468, which is congruent to insert 460.

Target 444 is coupled to clamp 442 by fitting socket 424 to plate 476 so that wall 496 mates with surface 474, and so that arcs 498 mate with indent 454. Once so coupled, target 444 may be held fixedly in place in any orientation selected by professional 22, by screwing a screw 472 into the female thread terminating indent 454.

During a procedure processor 26 is able to determine the orientation of the target, as a value between 0° and 360°, by imaging insert 460, and using the imaged insert as an optical indicator 462 of the orientation. In one embodiment processor 26 determines the orientation by finding the fraction of the insert visible through aperture 468, as well as a location of the visible insert.

In embodiments of the invention, the fraction may comprise a fractional area of the insert, or alternatively or additionally, a fractional linear dimension, such as an arc length, of the insert. In some embodiments the fractional linear dimension may be measured using a Vernier scale.

Thus, FIG. 7A illustrates a maximum of the insert visible through the aperture, corresponding to an orientation of 0°, and FIG. 7C illustrates a minimum of the insert visible through the aperture, corresponding to an orientation of 180°. FIG. 7B, corresponding to an orientation of 90° illustrates half of the insert visible, the visible half being located below the x-axis, and FIG. 7D, corresponding to an orientation of 270°, illustrates half of the insert visible, the visible half being located above the x-axis.

Other methods for determining the orientation of the target from the imaged insert, such as by finding coordinates of the endpoints of the imaged insert as well as coordinates of an intermediate point on the image, will be apparent, and all such methods are assumed to be comprised within the scope of the present invention.

During a procedure, processor 26 determines the orientation of target 444 from imaging optical indicator 462, as described above. The flowchart of FIG. 8 below describes how the processor uses the values of the orientation during the procedure.

Figure 8:
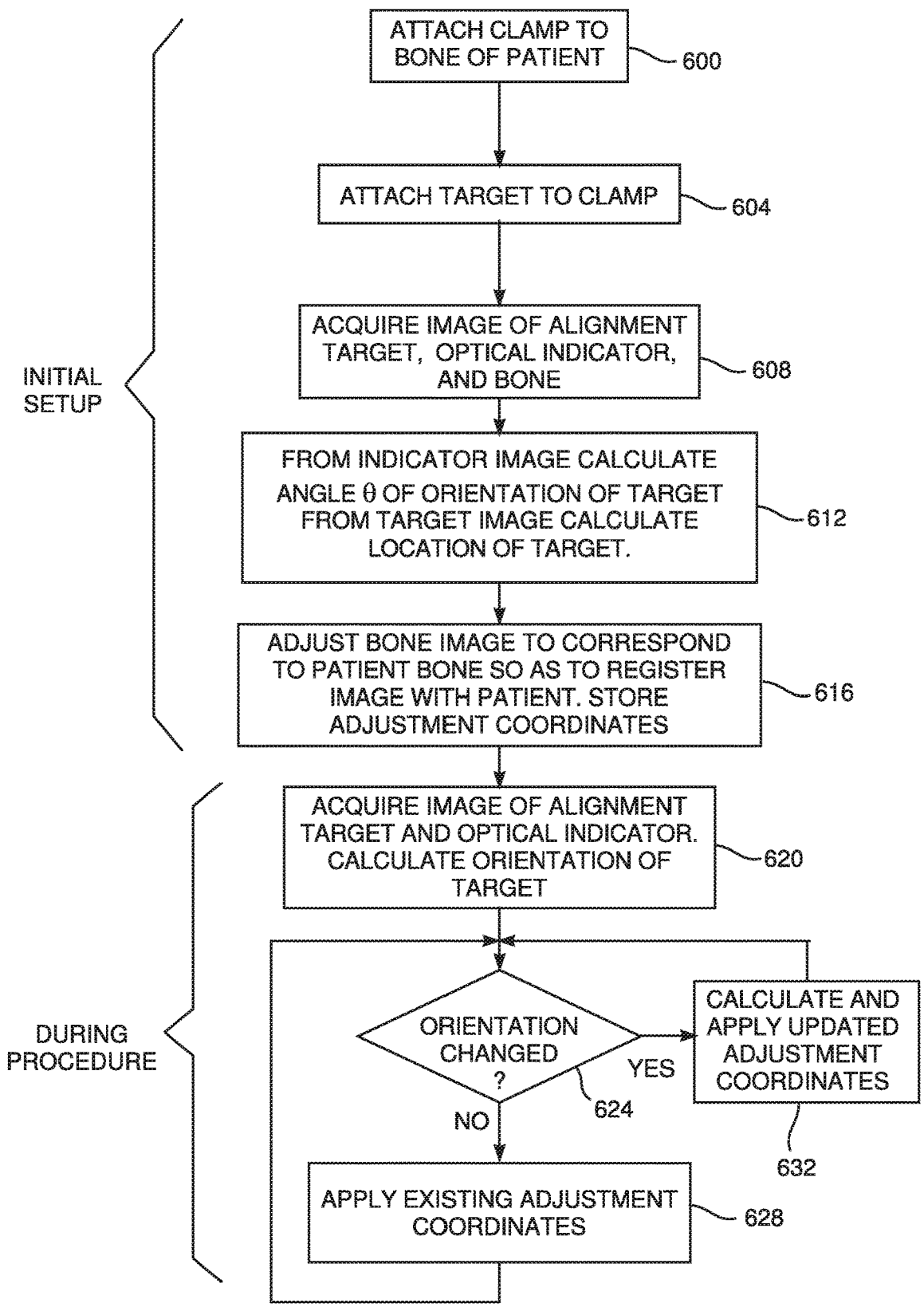
FIG. 8 is a flowchart describing the use of the marker of FIGS. 7A-7E, according to an embodiment of the present invention.
Figure 9:
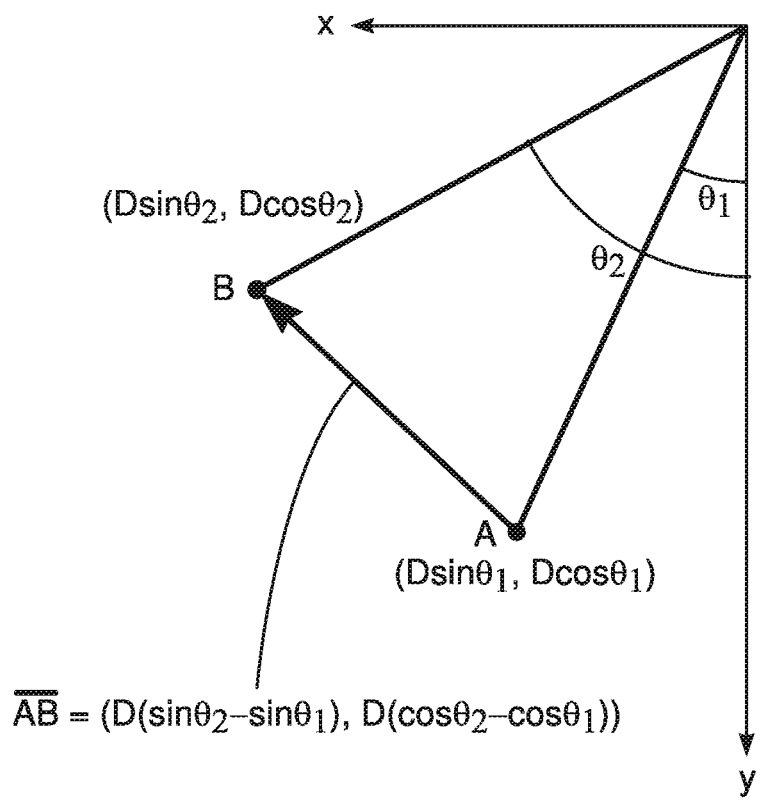
FIG. 9 is a diagram explaining some of the steps of the flowchart of FIG. 8, according to an embodiment of the present invention.

FIG. 8 is a flowchart describing the use of marker 440 in the medical procedure referred to above, and FIG. 9 is a diagram explaining some of the steps of the flowchart, according to an embodiment of the present invention.

An initial step 600, wherein clamp 442 is attached to the patient's bone, is substantially similar to initial step 200, described above.

In an attachment step 604, professional 22 attaches socket 424 to base 494, in any convenient orientation of target 444 to clamp 442. The professional uses screw 472 to fix the target to the clamp base.

An imaging step 608 is substantially similar to step 208, described above.

In an analysis step 612, the processor analyzes the image of indicator 462, as described above with reference to FIG. 7E, to determine an angle of orientation θ of the target with clamp 42. In addition, the processor calculates coordinates of the location of target region 120 from the image of the region acquired in step 608.

An adjustment step 616 is substantially as described above for step 216. Thus, in step 616 22 professional adjusts coordinates of a presented image to correspond with an actual image visible to the professional through augmented reality assembly 24. Processor 26 stores the adjustment coordinates, and applies the stored coordinates as an adjustment vector so as to register and track the presented image with patient 30.

Steps 600-616 correspond to an initial setup of navigation system 20 for marker 440. Steps 620-632, described below, correspond to steps of the flowchart that may be implemented during the medical procedure for which system 20 is used.

In a continuing imaging step 620, the processor, in addition to acquiring an image of patient 30, acquires an image of target 444, including target region 120 and indicator 462. From the image of indicator 462, the processor calculates an angle θ of the orientation of target region 120 relative to the clamp.

In a decision step 624 the processor checks if the angle calculated in step 620 is different from that calculated in step 612, so as to check if the target region has changed orientation. If the decision returns negative, i.e., there is no change in orientation, then in a continuation step 628 the processor continues to use the existing adjustment coordinates, i.e., those of step 616, as an adjustment vector.

If decision 624 returns positive, i.e., there is a change of orientation, then in an update step 632 the processor calculates a change-of-orientation vector, to be added to the existing adjustment vector, so as to enable the processor to maintain registration of images of patient 30 with the patient.

FIG. 9 is a schematic diagram illustrating how the processor calculates the change-of-orientation vector, according to an embodiment of the present invention. A line segment PA, having a length D, represents an initial orientation of adjustment target 444, where A is the center of region 120 and $\theta_1$ is the orientation of the center, both values being measured in step 612. A has coordinates $(D \sin \theta_1, D \cos \theta_1)$.

A line segment PB, having a length D, represents a subsequent orientation of adjustment target 444, where B is the center of region 120 and $\theta_2$ is the orientation of the center, both values being measured in step 620. B has coordinates $(D \sin \theta_2, D \cos \theta_2)$.

Processor 26 calculates a change-of-orientation vector [AB] as the difference between the coordinates of B and the coordinates of A, as in equation (1):

$$[AB] = (D(\sin \theta_2 - \sin \theta_1), D(\cos \theta_2 - \cos \theta_1)) \quad (1)$$

Returning to the flowchart of FIG. 8, in step 632 the processor adds a change-of-orientation vector, calculated as described for equation (1), to the existing adjustment vector.

From steps 628 and 632 control returns to decision step 624, so that during the procedure the processor applies steps 624-632 iteratively.

A positive return of decision 624 is typically caused by professional 22 changing the orientation of target 444 by loosening then tightening screw 472. In some embodiments the professional may pause processor 26 tracking target 444 while positioning the target in a new orientation. It will be understood that there is no need to repeat steps 600-620 after any re-orientation, since by iterating steps 624-632 the processor continues to correctly register any acquired image of patient 30 with the patient.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A marker for image guided surgery, comprising:
   a base, having a base axis, connecting to a clamp; and
   an alignment target, comprising:
      a target region having an alignment pattern formed thereon;
      a socket connected to the target region and configured to fit rotatably to the base, whereby the alignment target is rotatable about the base axis; and
      an optical indicator for the socket indicating an angle of orientation of the alignment target about the base axis.

2. The marker according to claim 1, wherein the socket is configured to only fit to the base in a plurality of at least two discrete orientations about the base axis.

3. The marker according to claim 2, wherein the plurality of discrete configurations is distributed symmetrically about the base axis.

4. The marker according to claim 2, wherein the plurality comprises four discrete orientations.

5. The marker according to claim 2, wherein the socket comprises a plurality of apertures equal to the plurality of discrete orientations, and wherein the optical indicator is configured to be visible through one of the apertures indicative of one of the discrete orientations.

6. The marker according to claim 2, wherein the socket comprises a plurality of apertures equal to the plurality of discrete orientations, and wherein the optical indicator is configured to be visible through apertures selected and arranged so as to provide an unambiguous identification of each of the discrete orientations.

7. The marker according to claim 1, wherein the socket is configured to fit to the base in a plurality of non-discrete orientations about the base axis.

8. The marker according to claim 7, wherein the socket comprises an aperture, and wherein the optical indicator is congruent with the aperture, and wherein a fraction of the optical indicator visible through the aperture is indicative of one of the non-discrete orientations.

9. The marker according to claim 8, wherein the aperture comprises a semicircular arc.

10. The marker according to claim 1, wherein the socket is at a fixed distance from the target region, the marker further comprising:
an augmented reality system operative during surgery on a patient; and
a processor configured to:
track the alignment target during the surgery,
provide a patient tracking vector to the augmented reality system in response to the tracking of the alignment target,
calculate a change in the angle of orientation of the alignment target in response to changes in images of the optical indicator, and
add a change-of-orientation vector, based only on the fixed distance and the change in the angle of orientation, to the patient tracking vector so as to update the patient tracking vector.

11. A method for enabling rotation of a marker during surgery without requiring re-registration, comprising:
connecting a base, having a base axis, to a clamp;
forming an alignment pattern on a target region of an alignment target;
connecting a socket to the target region, the socket being at a fixed distance from the target region and being configured to fit rotatably to the base, whereby the alignment target is rotatable about the base axis;
providing an optical indicator for the socket indicating an angle of orientation of the alignment target about the base axis;
operating an augmented reality system during the surgery on a patient;
tracking the alignment target during the surgery;
providing a patient tracking vector to the augmented reality system in response to the tracking of the alignment target;
calculating a change in the angle of orientation of the alignment target in response to changes in images of the optical indicator; and
adding a change-of-orientation vector, based only on the fixed distance and the change in the angle of orientation, to the patient tracking vector so as to update the patient tracking vector.

12. The method according to claim 11, wherein the socket is configured to only fit to the base in a plurality of at least two discrete orientations about the base axis.

13. The method according to claim 12, wherein the plurality of discrete configurations is distributed symmetrically about the base axis.

14. The method according to claim 12, wherein the plurality comprises four discrete orientations.

15. The method according to claim 12, wherein the socket comprises a plurality of apertures equal to the plurality of discrete orientations, and wherein the optical indicator is configured to be visible through one of the apertures indicative of one of the discrete orientations.

16. The method according to claim 12, wherein the socket comprises a plurality of apertures equal to the plurality of discrete orientations, and wherein the optical indicator is configured to be visible through apertures selected and arranged so as to provide an unambiguous identification of each of the discrete orientations.

17. The method according to claim 11, wherein the socket is configured to fit to the base in a plurality of non-discrete orientations about the base axis.

18. The method according to claim 17, wherein the socket comprises an aperture, and wherein the optical indicator is congruent with the aperture, and wherein a fraction of the optical indicator visible through the aperture is indicative of one of the non-discrete orientations.

19. The method according to claim 18, wherein the aperture comprises a semicircular arc.

* * * * *